United States Patent [19]
Griffiths et al.

[11] Patent Number: 6,010,884
[45] Date of Patent: Jan. 4, 2000

[54] RECOMBINANT BINDING PROTEINS AND PEPTIDES

[75] Inventors: Andrew David Griffiths; Kaspar Philipp Holliger; Ahuva Nissim, all of Cambridge; Igor Fisch, Coton; Gregory Paul Winter, Cambridge, all of United Kingdom

[73] Assignee: Medical Research Council, London, United Kingdom

[21] Appl. No.: 08/654,623

[22] Filed: May 29, 1996

Related U.S. Application Data

[63] Continuation of application No. PCT/GB94/02662, Dec. 5, 1994, and a continuation-in-part of application No. 08/448,418, May 14, 1996, Pat. No. 5,837,242.

[30] Foreign Application Priority Data

| Dec. 4, 1992 | [GB] | United Kingdom | 9225453 |
| Jan. 16, 1993 | [GB] | United Kingdom | 9300816 |
| May 10, 1993 | [EP] | European Pat. Off. | 93303614 |
| Sep. 22, 1993 | [GB] | United Kingdom | 9319969 |
| Jun. 17, 1994 | [GB] | United Kingdom | 9412147 |

[51] Int. Cl.$^7$ .............................. C07K 19/00; C12N 15/62
[52] U.S. Cl. .................. 435/69.7; 435/172.3; 435/252.3; 435/320.1; 536/23.4
[58] Field of Search .................................. 435/69.1, 69.7, 435/69.8, 172.3, 252.3, 254.11, 320.1, 325; 536/23.4, 23.53, 24.1

[56] References Cited

U.S. PATENT DOCUMENTS

| 5,196,320 | 3/1993 | Gillies | 435/69.7 |
| 5,434,066 | 7/1995 | Bebee et al. | 435/172.3 |
| 5,534,254 | 7/1996 | Huston et al. | 424/135.1 |
| 5,641,673 | 6/1997 | Haseloff et al. | 435/325 |

FOREIGN PATENT DOCUMENTS

| WO 88/06630 | 9/1988 | WIPO | C12P 21/00 |
| WO 93/11236 | 6/1993 | WIPO . | |
| WO 93/17116 | 9/1993 | WIPO . | |
| WO 93/19172 | 9/1993 | WIPO . | |

OTHER PUBLICATIONS

Cech, T. R., "RNA Splicing: Three Themes with Variations," *Cell*, 34:713–716 (Oct., 1983).

Hoess et al., "P1 Site–Specific Recombination: Nucleotide Sequence of the Recombining Sites," *Proc. Nat'l Acad. Sci., USA*, 79:3398–3402 (Jun., 1982).

Hoess et al., "The Role of the loxP Spacer Region in P1 Site–Specific Recombination," *Nucleic Acids Research*, 14(5):2287–2300 (1986).

Huston et al., "Protein Engineering of Antibody Binding Sites: Recovery of Specific Activity in an Anti–Digoxin Single–Chain Fv Analogue Produced in *Escherichia coli*," *Proc. Nat'l Acad. Sci., USA*, 85:5879–5883 (Aug., 1988).

Mörl et al., "Group II Intron RNA–Catalyzed Recombination of RNA in vitro," *Nucleic Acids Research*, 18(22):6545–6550 (1990).

Waterhouse et al., "Combinatorial Infection and In Vivo Recombination: A Strategy for Making Large Phage Antibody Repertoires," *Nucleic Acids Research*, 21(9):2265–2266 (1993).

Huston et al. Portein engineering of single–chain Fv analogs and fusion proteins. Methods in Enzymology, Langone, ed. Academic Press, Inc., NY. vol. 203, pp. 46–88, 1991.

Waring et al. "The Tetrahymena rRNA Intron Self–Splices in *E. Coli*: In Vivo Evidence for the Importance of Key Base–Paired Regions of RNA Enzyme Function". Cell 40(2):371–380, Feb. 1985.

Devlin et al. "Random Peptide Libraries: A Source of Specific Protein Binding Molecules". Science 249:404–406, Jul. 1990.

*Primary Examiner*—John Ulm
*Attorney, Agent, or Firm*—Marshall, O'Toole, Gerstein, Murray & Borun

[57] ABSTRACT

DNA constructs comprise a first exon sequence of nucleotides encoding a first peptide or polypeptide, a second exon sequence of nucleotides encoding a second peptide or polypeptide and a third sequence of nucleotides between the first and second sequences encoding a heterologous intron, for example that of *Tetrahymena thermophila* nuclear pre-rRNA, between RNA splice sites and a site-specific recombination sequence, such as loxP, within the intron, the exons together encoding a product peptide or polypeptide. Such constructs are of use in methods of production of peptides or polypeptides, transcription leading to splicing out of the intron enabling translation of a single chain product peptide or polypeptide. Isolated nucleic acid constructs consisting essentially of a sequence of nucleotides encoding a self-splicing intron with a site-specific recombination sequence within the intron, for use in creation of constructs for expression of peptides or polypeptides, are also provided.

50 Claims, 13 Drawing Sheets

Fig.1.

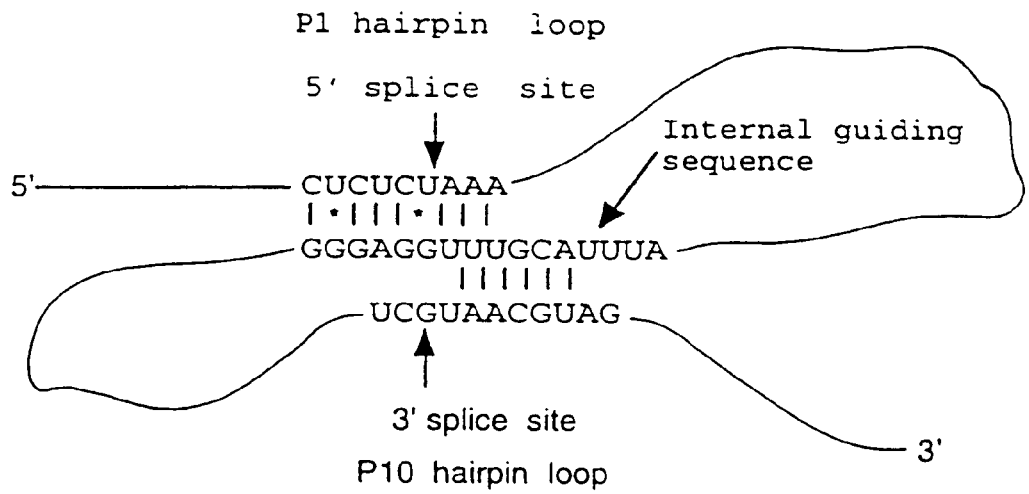

P1 hairpin loop
5' splice site
Internal guiding sequence
3' splice site
P10 hairpin loop

Fig.4.

lox P (wt) wild type

ATAACTTCGTATA ATGTATGC TATACGAAGTTAT lox P 511

ATAACTTCGTATA ATGTATAC TATACGAAGTTAT lox P 3

ATAACTTCGTATA ACATACCC TATACGAAGTTAT lox P1

ATAACTTCGTATA ATATAAAC TATACGAAGTTAT lox P2

ATAACTTCGTATA ATCTAACC TATACGAAGTTAT lox P4

ATAACTTCGTATA ACATAGCC TATACGAAGTTAT

Fig.2.
(a) 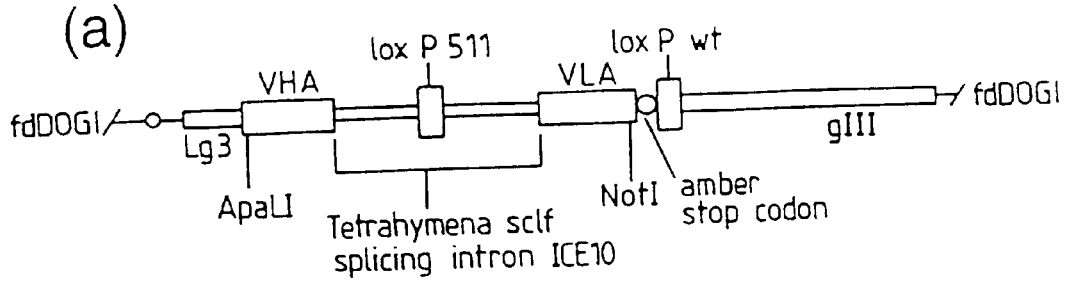
(b) 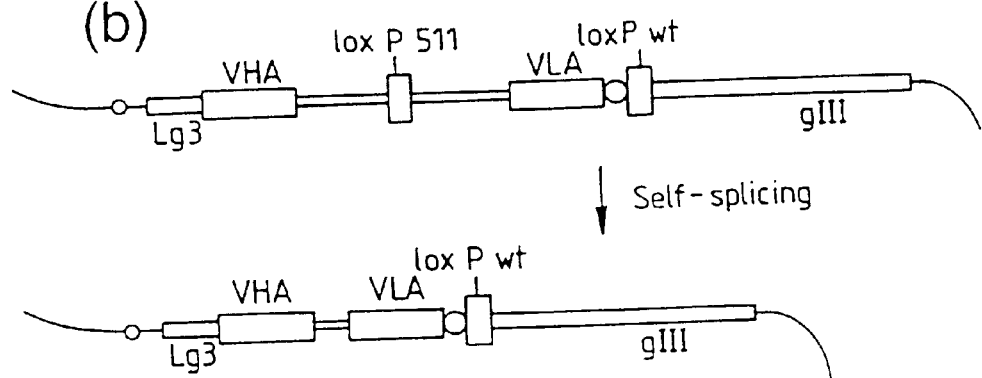
(c) 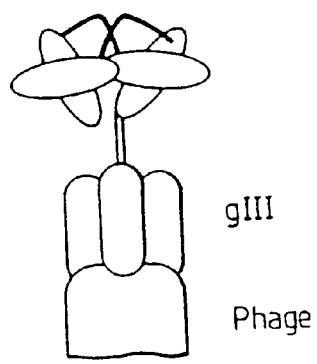

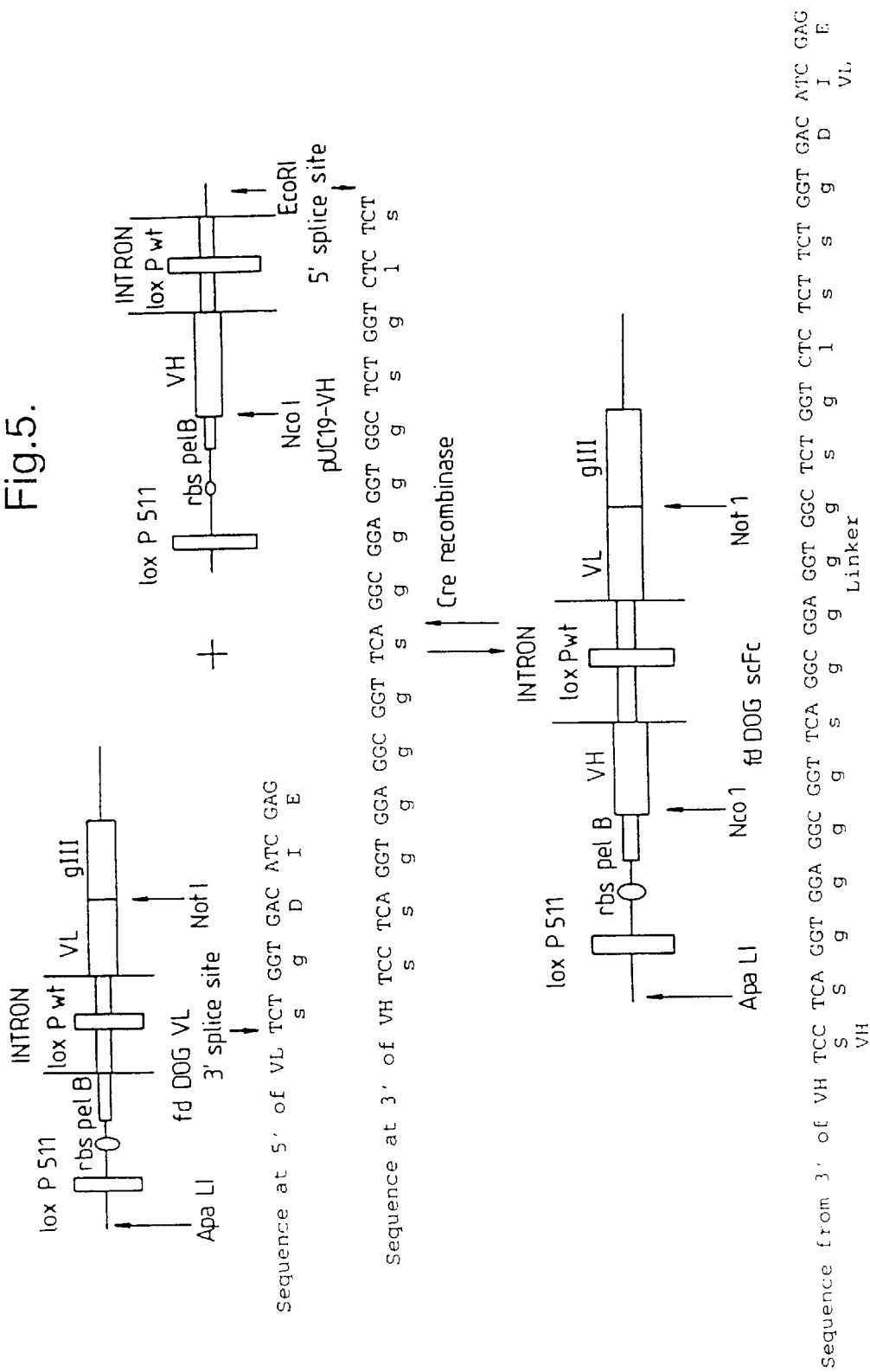

Fig. 7.
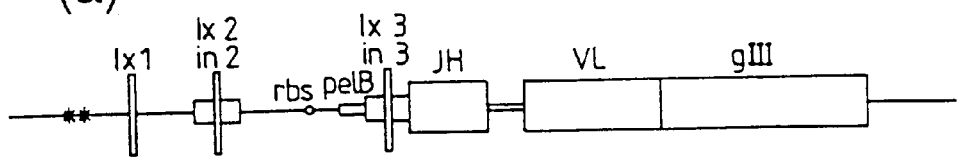
(a)
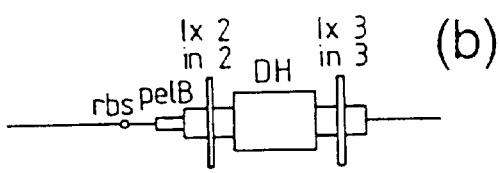
(b)
Cre recombinase
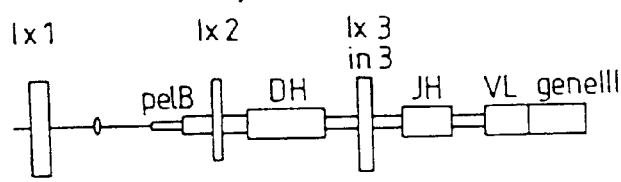
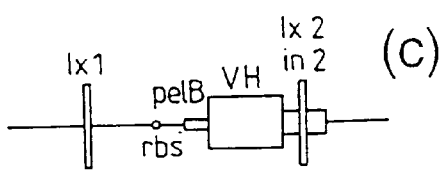
(c)
Cre recombinase
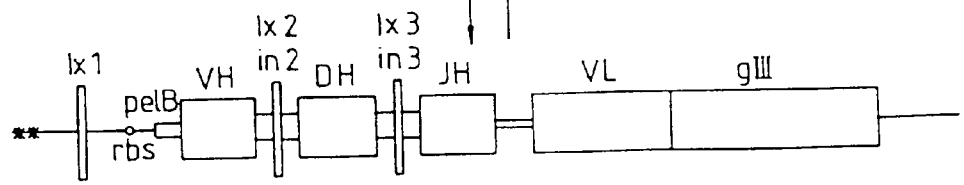
(d)

Fig. 8.
(a)
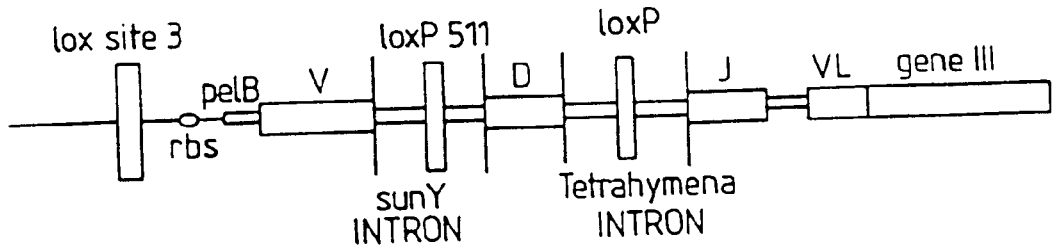
(b)
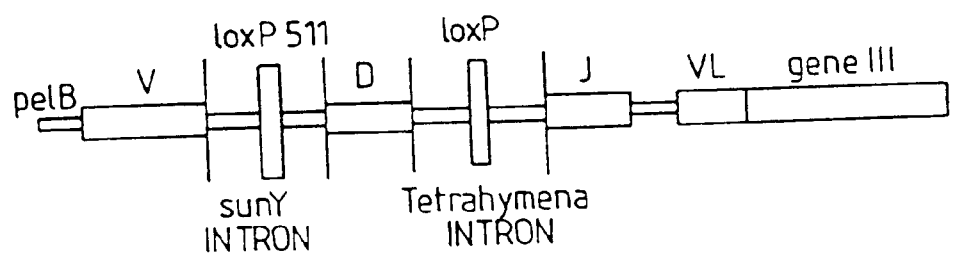
(c)
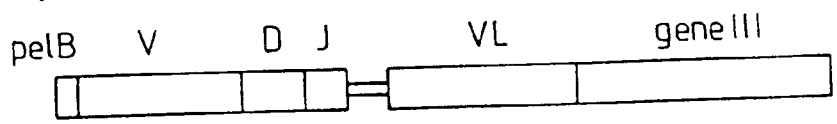
(d)
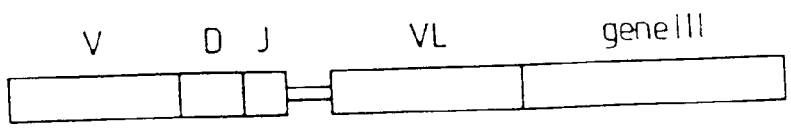

Fig.9.
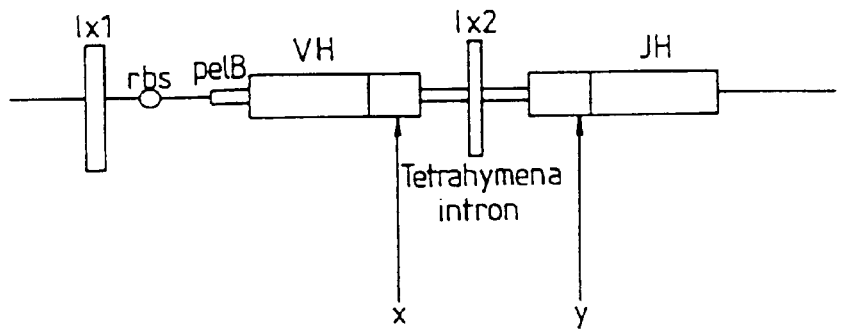
Fig.13.
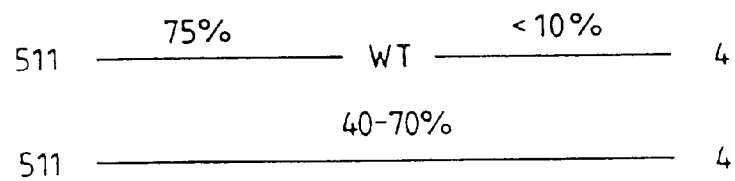
(b)
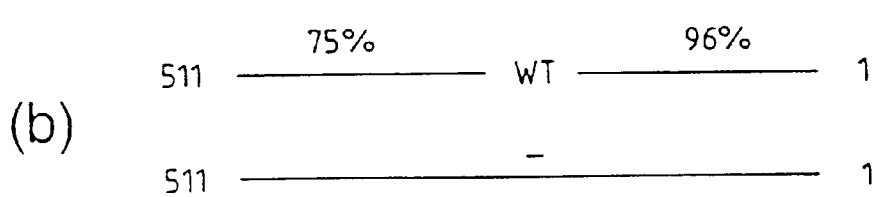
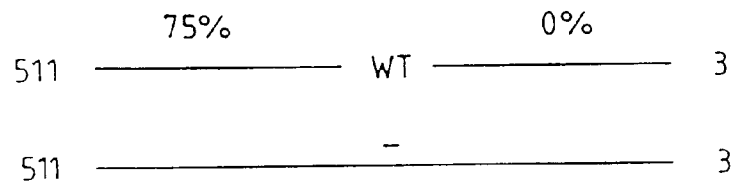

Fig.10.
(a)
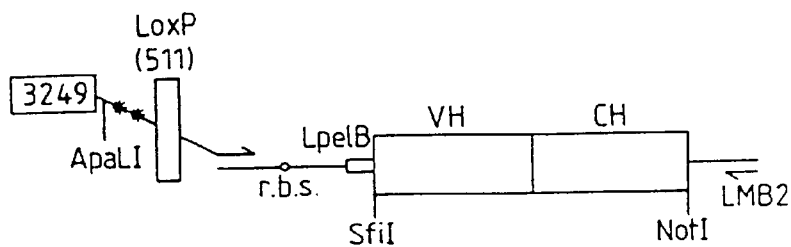
(b)
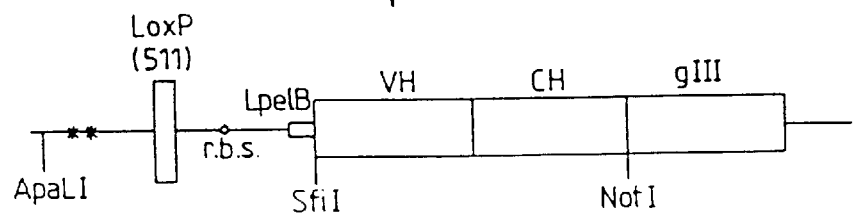
(c)
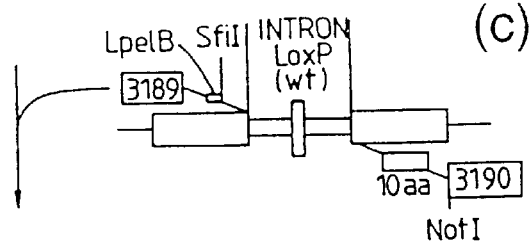
(d)
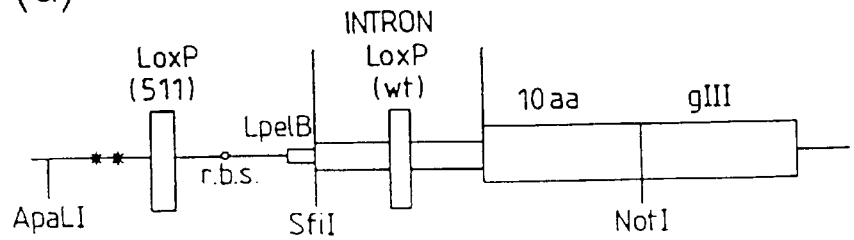

Fig.11.
(a)
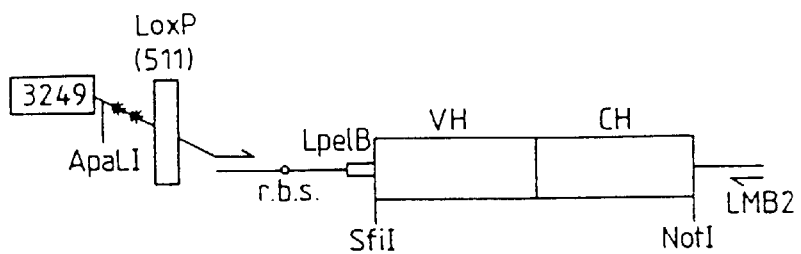
(b)
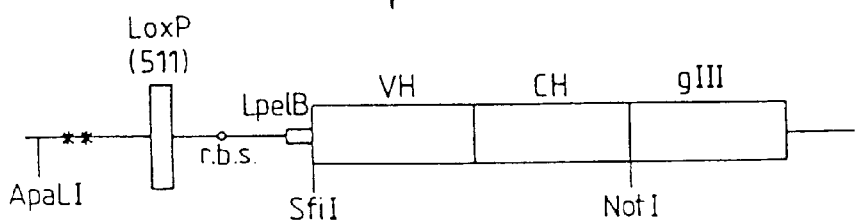
(c)
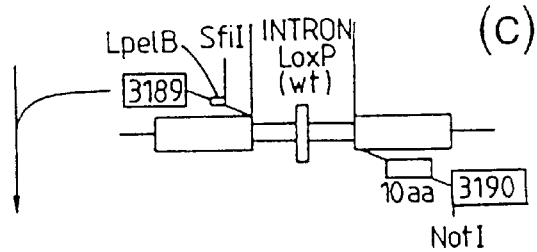
(d)
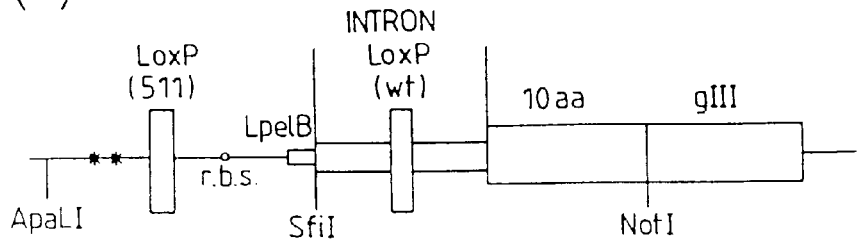

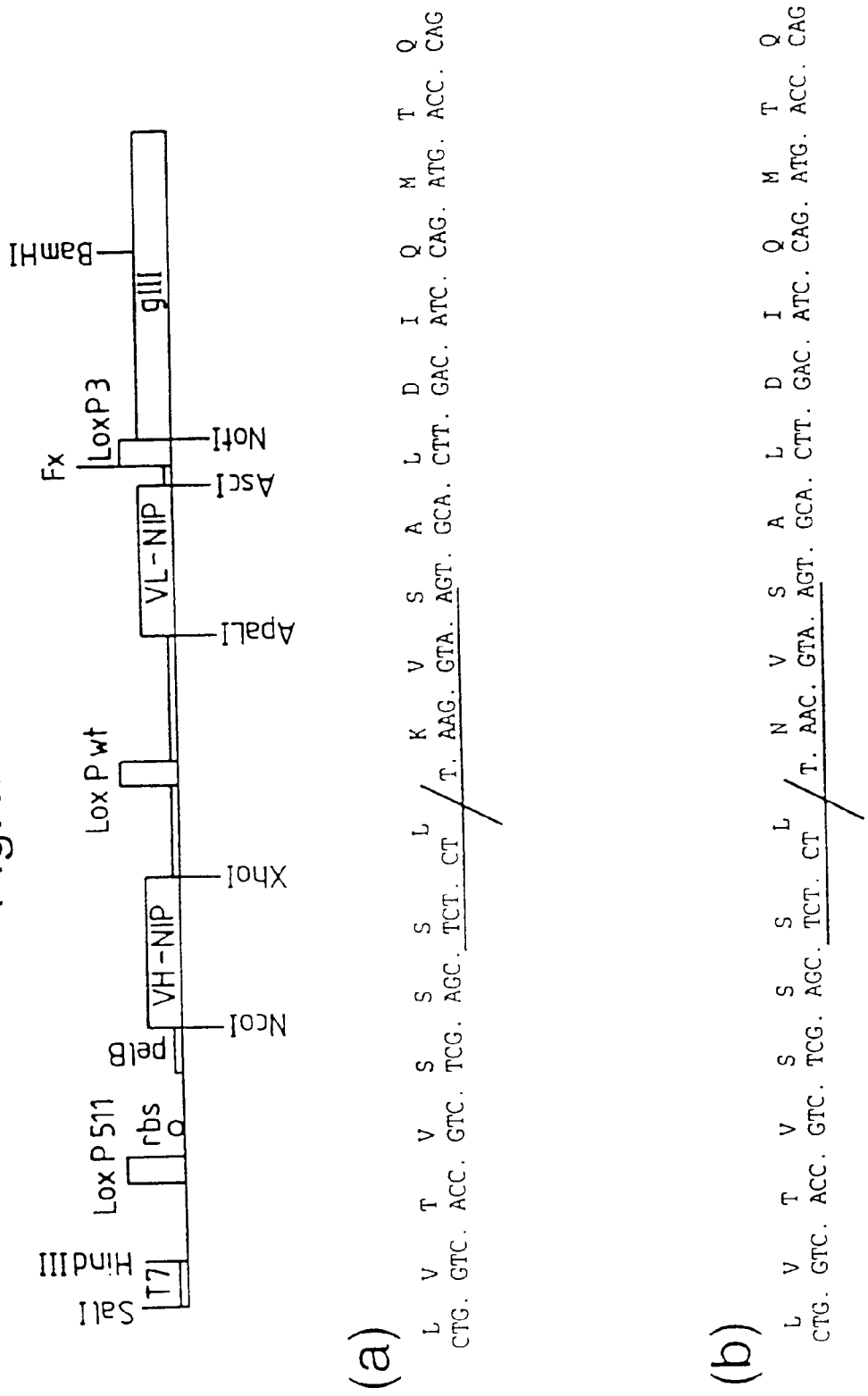

```
  L    V    T    V    S    S    g    g    g    c    l
CTG. GTC. ACC. GTC. TCG. AGC. ggc. gga. ggt. ggC. TCT. CT
                                    Spliced Intron
  n    v    g    g    g    g    s    a    I    D    I    Q    M    T    Q
T. AAC. GTA. ggt. gga. ggc. ggt. AGT. GCA. CTT. GAC. ATC. CAG. ATG. ACC. CAG
```

(d)

```
         P1                                              P10
              A G C A
         CUCUCUAAA U G     A U
         |*|||*|||      A
         GGGAGGUUUCCAUUU A
         |||||||||
         GTAAGGTA
                    →
                    C
```

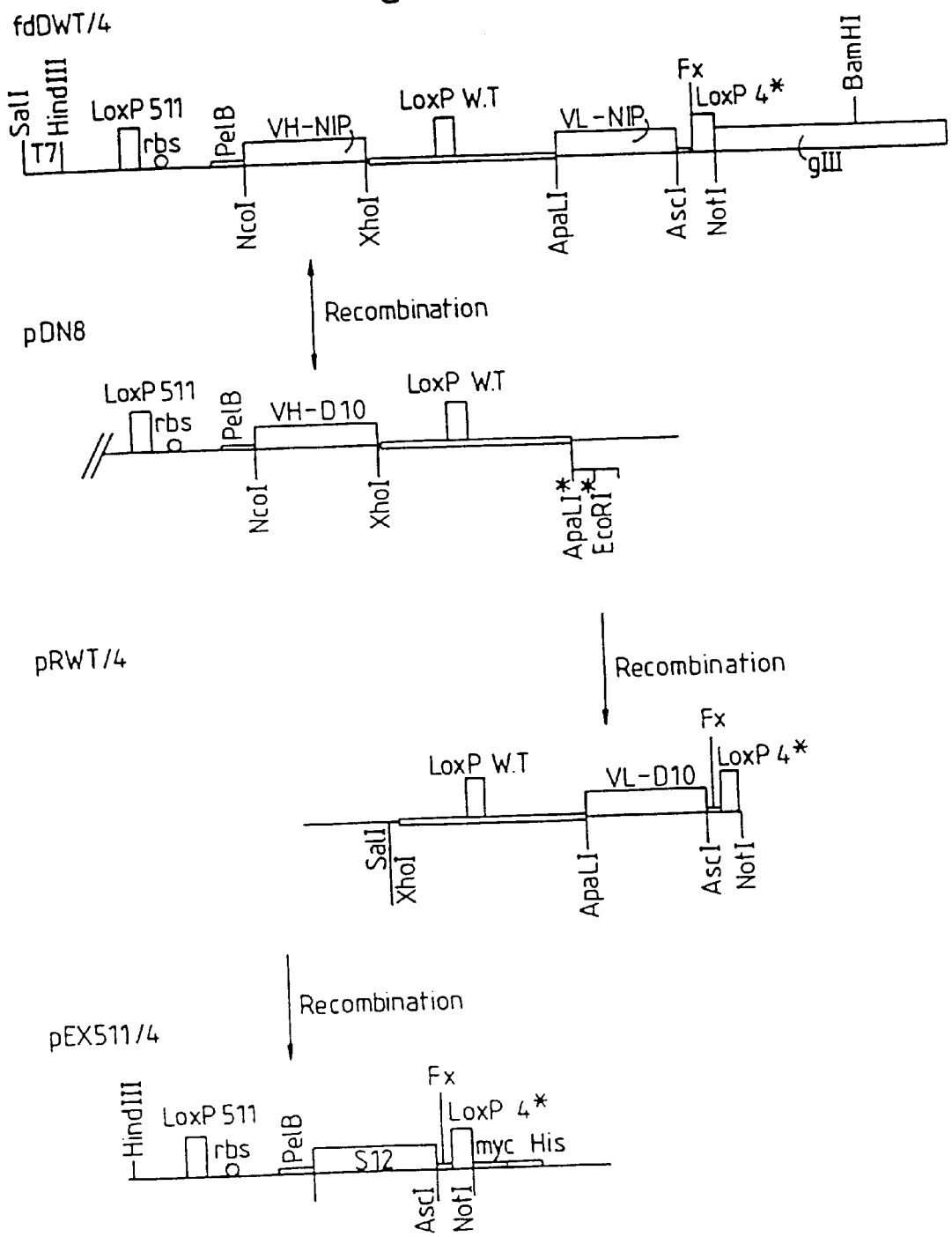
(a) Fig. 13.

SEQUENCE LISTING (1) GENERAL INFORMATION:

(iii) NUMBER OF SEQUENCES: 71

(2) INFORMATION FOR SEQ ID NO:1:

(i) SEQUENCE CHARACTERISTICS:
      (A) LENGTH: 9 base pairs
      (B) TYPE: nucleic acid
      (C) STRANDEDNESS: single
      (D) TOPOLOGY: linear (ii) MOLECULE TYPE: mRNA (xi) SEQUENCE DESCRIPTION: SEQ ID NO:1:

CUCUCUAAA                                           9

(2) INFORMATION FOR SEQ ID NO:2:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: mRNA (xi) SEQUENCE DESCRIPTION: SEQ ID NO:2:

AUUUACGUUU GGAGGG                              16

```
(2) INFORMATION FOR SEQ ID NO:3:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:3:

UCGUAACGUA G                                                              11

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: double
        (D) TOPOLOGY: circular (ii) MOLECULE TYPE: Other nucleic acid: plasmid DNA (xi) SEQUENCE DESCRIPTION: SEQ ID NO:4:

ATAACTTCGT ATAATGTATG CTATACGAAG TTAT                                     34

(2) INFORMATION FOR SEQ ID NO:5:

(i) SEQUENCE CHARACTERISTICS:
        (A) LENGTH: 34 base pairs
        (B) TYPE: nucleic acid
        (C) STRANDEDNESS: double
        (D) TOPOLOGY: circular (ii) MOLECULE TYPE: Other nucleic acid: plasmid DNA (xi) SEQUENCE DESCRIPTION: SEQ ID NO:5:

ATAACTTCGT ATAATGTATA CTATACGAAG TTAT                                     34

(2) INFORMATION FOR SEQ ID NO:6:

(i) SEQUENCE CHARACTERISTICS:
        (A) LENGTH: 34 base pairs
        (B) TYPE: nucleic acid
        (C) STRANDEDNESS: double
        (D) TOPOLOGY: circular (ii) MOLECULE TYPE: Other nucleic acid: plasmid DNA (xi) SEQUENCE DESCRIPTION: SEQ ID NO:6:

ATAACTTCGT ATAACATACC CTATACGAAG TTAT                                     34

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: double
        (D) TOPOLOGY: circular (ii) MOLECULE TYPE: Other nucleic acid: plasmid DNA (xi) SEQUENCE DESCRIPTION: SEQ ID NO:7:

ATAACTTCGT ATAATATAAA CTATACGAAG TTAT                                     34

(2) INFORMATION FOR SEQ ID NO:8:

(i) SEQUENCE CHARACTERISTICS:
        (A) LENGTH: 34 base pairs
        (B) TYPE: nucleic acid
```

(C) STRANDEDNESS: double
            (D) TOPOLOGY: circular (ii) MOLECULE TYPE: Other nucleic acid: plasmid DNA (xi) SEQUENCE DESCRIPTION: SEQ ID NO:8:

ATAACTTCGT ATAATCTAAC CTATACGAAG TTAT                                 34

(2) INFORMATION FOR SEQ ID NO:9:

(i) SEQUENCE CHARACTERISTICS:
            (A) LENGTH: 34 base pairs
            (B) TYPE: nucleic acid
            (C) STRANDEDNESS: double
            (D) TOPOLOGY: circular (ii) MOLECULE TYPE: Other nucleic acid: plasmid DNA (xi) SEQUENCE DESCRIPTION: SEQ ID NO:9:

ATAACTTCGT ATAACATAGC CTATACGAAG TTAT                                 34

(2) INFORMATION FOR SEQ ID NO:10:

(i) SEQUENCE CHARACTERISTICS:
            (A) LENGTH: 15 base pairs
            (B) TYPE: nucleic acid
            (C) STRANDEDNESS: double
            (D) TOPOLOGY: circular (ii) MOLECULE TYPE: Other nucleic acid: chimaeric DNA (ix) FEATURE:
            (A) NAME/KEY: CDS
            (B) LOCATION: 1..15

(xi) SEQUENCE DESCRIPTION: SEQ ID NO:10:

TCT GGT GAC ATC GAG                                                   15
Ser Gly Asp Ile Glu
 1               5

(2) INFORMATION FOR SEQ ID NO:11:

(i) SEQUENCE CHARACTERISTICS:
            (A) LENGTH: 5 amino acids
            (B) TYPE: amino acid
            (D) TOPOLOGY: linear (ii) MOLECULE TYPE: protein (xi) SEQUENCE DESCRIPTION: SEQ ID NO:11:

Ser Gly Asp Ile Glu
 1               5

(2) INFORMATION FOR SEQ ID NO:12:

(i) SEQUENCE CHARACTERISTICS:
            (A) LENGTH: 45 base pairs
            (B) TYPE: nucleic acid
            (C) STRANDEDNESS: double
            (D) TOPOLOGY: circular (ii) MOLECULE TYPE: Other nucleic acid: chimaeric DNA (ix) FEATURE:
            (A) NAME/KEY: CDS
            (B) LOCATION: 1..45

(xi) SEQUENCE DESCRIPTION: SEQ ID NO:12:

TCC TCA GGT GGA GGC GGT TCA GGC GGA GGT GGC TCT GGT CTC TCT           45
Ser Ser Gly Gly Gly Gly Ser Gly Gly Gly Gly Ser Gly Leu Ser
 1               5                  10                  15

(2) INFORMATION FOR SEQ ID NO:13:

(i) SEQUENCE CHARACTERISTICS:
        (A) LENGTH: 15 amino acids
        (B) TYPE: amino acid
        (D) TOPOLOGY: linear (ii) MOLECULE TYPE: protein (xi) SEQUENCE DESCRIPTION: SEQ ID NO:13:

```
Ser Ser Gly Gly Gly Gly Ser Gly Gly Gly Gly Ser Gly Leu Ser
 1               5                  10                  15
```

(2) INFORMATION FOR SEQ ID NO:14:

(i) SEQUENCE CHARACTERISTICS:
        (A) LENGTH: 60 base pairs
        (B) TYPE: nucleic acid
        (C) STRANDEDNESS: double
        (D) TOPOLOGY: circular (ii) MOLECULE TYPE: Other nucleic acid: chimaeric DNA (ix) FEATURE:
        (A) NAME/KEY: CDS
        (B) LOCATION: 1..60

(xi) SEQUENCE DESCRIPTION: SEQ ID NO:14:

```
TCC TCA GGT GGA GGC GGT TCA GGC GGA GGT GGC TCT GGT CTC TCT TCT        48
Ser Ser Gly Gly Gly Gly Ser Gly Gly Gly Gly Ser Gly Leu Ser Ser
 1               5                  10                  15

GGT GAC ATC GAG                                                        60
Gly Asp Ile Glu
            20
```

(2) INFORMATION FOR SEQ ID NO:15:

(i) SEQUENCE CHARACTERISTICS:
        (A) LENGTH: 20 amino acids
        (B) TYPE: amino acid
        (D) TOPOLOGY: linear (ii) MOLECULE TYPE: protein (xi) SEQUENCE DESCRIPTION: SEQ ID NO:15:

```
Ser Ser Gly Gly Gly Gly Ser Gly Gly Gly Gly Ser Gly Leu Ser Ser
 1               5                  10                  15

Gly Asp Ile Glu
            20
```

(2) INFORMATION FOR SEQ ID NO:16:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Gly Leu Ser Ser Gly
 1               5
```

(2) INFORMATION FOR SEQ ID NO:17:

(i) SEQUENCE CHARACTERISTICS:
        (A) LENGTH: 25 amino acids

```
              (B) TYPE: amino acid
              (C) STRANDEDNESS: single
              (D) TOPOLOGY: linear (ii) MOLECULE TYPE: peptide (ix) FEATURE:
              (B) LOCATION: 1..10
              (D) OTHER INFORMATION: /note= "Xaa is any amino acid
                  encoded by NNK"

(ix) FEATURE:
              (B) LOCATION: 16..25
              (D) OTHER INFORMATION: /note= "Xaa is any amino acid
                  encoded by NNK"

(xi) SEQUENCE DESCRIPTION: SEQ ID NO:17:

Xaa Xaa Xaa Xaa Xaa Xaa Xaa Xaa Xaa Xaa Ala Leu Leu Arg Tyr Xaa
1               5                  10                  15

Xaa Xaa Xaa Xaa Xaa Xaa Xaa Xaa Xaa
            20                  25

(2) INFORMATION FOR SEQ ID NO:18:

(i) SEQUENCE CHARACTERISTICS:
              (A) LENGTH: 57 base pairs
              (B) TYPE: nucleic acid
              (C) STRANDEDNESS: double
              (D) TOPOLOGY: circular (ii) MOLECULE TYPE: Other nucleic acid: chimaeric DNA (ix) FEATURE:
              (A) NAME/KEY: CDS
              (B) LOCATION: 1..57

(xi) SEQUENCE DESCRIPTION: SEQ ID NO:18:

CTG GTC ACC GTC TCG AGC TCT CTT AAG GTA AGT GCA CTT GAC ATC CAG      48
Leu Val Thr Val Ser Ser Ser Leu Lys Val Ser Ala Leu Asp Ile Gln
1               5                  10                  15

ATG ACC CAG                                                          57
Met Thr Gln (2) INFORMATION FOR SEQ ID NO:19:

(i) SEQUENCE CHARACTERISTICS:
              (A) LENGTH: 19 amino acids
              (B) TYPE: amino acid
              (D) TOPOLOGY: linear (ii) MOLECULE TYPE: protein (xi) SEQUENCE DESCRIPTION: SEQ ID NO:19:

Leu Val Thr Val Ser Ser Ser Leu Lys Val Ser Ala Leu Asp Ile Gln
1               5                  10                  15

Met Thr Gln (2) INFORMATION FOR SEQ ID NO:20:

(i) SEQUENCE CHARACTERISTICS:
              (A) LENGTH: 57 base pairs
              (B) TYPE: nucleic acid
              (C) STRANDEDNESS: double
              (D) TOPOLOGY: circular (ii) MOLECULE TYPE: Other nucleic acid: chimaeric DNA (ix) FEATURE:
              (A) NAME/KEY: CDS
              (B) LOCATION: 1..57
```

(xi) SEQUENCE DESCRIPTION: SEQ ID NO:20:

CTG GTC ACC GTC TCG AGC TCT CTT AAC GTA AGT GCA CTT GAC ATC CAG        48
Leu Val Thr Val Ser Ser Ser Leu Asn Val Ser Ala Leu Asp Ile Gln
1               5                   10                  15

ATG ACC CAG                                                            57
Met Thr Gln (2) INFORMATION FOR SEQ ID NO:21:

(i) SEQUENCE CHARACTERISTICS:
        (A) LENGTH: 19 amino acids
        (B) TYPE: amino acid
        (D) TOPOLOGY: linear (ii) MOLECULE TYPE: protein (xi) SEQUENCE DESCRIPTION: SEQ ID NO:21:

Leu Val Thr Val Ser Ser Ser Leu Asn Val Ser Ala Leu Asp Ile Gln
1               5                   10                  15

Met Thr Gln (2) INFORMATION FOR SEQ ID NO:22:

(i) SEQUENCE CHARACTERISTICS:
        (A) LENGTH: 81 base pairs
        (B) TYPE: nucleic acid
        (C) STRANDEDNESS: double
        (D) TOPOLOGY: circular (ii) MOLECULE TYPE: Other nucleic acid: chimaeric DNA (ix) FEATURE:
        (A) NAME/KEY: CDS
        (B) LOCATION: 1..81

(xi) SEQUENCE DESCRIPTION: SEQ ID NO:22:

CTG GTC ACC GTC TCG AGC GGC GGA GGT GGC TCT CTT AAC GTA GGT GGA        48
Leu Val Thr Val Ser Ser Gly Gly Gly Gly Ser Leu Asn Val Gly Gly
1               5                   10                  15

GGC GGT AGT GCA CTT GAC ATC CAG ATG ACC CAG                            81
Gly Gly Ser Ala Leu Asp Ile Gln Met Thr Gln
            20                  25

(2) INFORMATION FOR SEQ ID NO:23:

(i) SEQUENCE CHARACTERISTICS:
        (A) LENGTH: 27 amino acids
        (B) TYPE: amino acid
        (D) TOPOLOGY: linear (ii) MOLECULE TYPE: protein (xi) SEQUENCE DESCRIPTION: SEQ ID NO:23:

Leu Val Thr Val Ser Ser Gly Gly Gly Gly Ser Leu Asn Val Gly Gly
1               5                   10                  15

Gly Gly Ser Ala Leu Asp Ile Gln Met Thr Gln
            20                  25

(2) INFORMATION FOR SEQ ID NO:24:

(i) SEQUENCE CHARACTERISTICS:
        (A) LENGTH: 32 base pairs
        (B) TYPE: nucleic acid
        (C) STRANDEDNESS: single
        (D) TOPOLOGY: linear

```
       (ii) MOLECULE TYPE: mRNA (xi) SEQUENCE DESCRIPTION: SEQ ID NO:24:

CUCUCUAAAU AGCAAUAUUU ACCUUUGGAG GG                              32

(2) INFORMATION FOR SEQ ID NO:25:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO:25:

CUCUCUAAAU AGCAAUAUUU ACGUUUGGAG GG                              32

(2) INFORMATION FOR SEQ ID NO:26:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO:26:

GUAAGGUA                                                          8

(2) INFORMATION FOR SEQ ID NO:27:

(i) SEQUENCE CHARACTERISTICS:
            (A) LENGTH: 8 base pairs
            (B) TYPE: nucleic acid
            (C) STRANDEDNESS: single
            (D) TOPOLOGY: linear (ii) MOLECULE TYPE: mRNA (xi) SEQUENCE DESCRIPTION: SEQ ID NO:27:

GUAACGUA                                                          8

(2) INFORMATION FOR SEQ ID NO:28:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:28:

Gly Ser Leu Lys Val Gly
1               5

(2) INFORMATION FOR SEQ ID NO:29:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:29:
```

```
Gly Gly Gly Gly Ser Gly Gly Gly Ser Gly Leu Ser Ser Gly
1               5               10              15
```

(2) INFORMATION FOR SEQ ID NO:30:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:30:

GAGCCATCAA TCTCGGAGCT CGATGTCACC TACCTTACGA GTACTCCAAA ACTAATCA      58

(2) INFORMATION FOR SEQ ID NO:31:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:31:

CCATCAATCG ATCTGGTCAC CGTCTCCTCA GGCTCTCTAA ATAGCAATAT TTACCT      56

(2) INFORMATION FOR SEQ ID NO:32:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:32:

GAGCCATCAA TCTCGGAGCT CGATGTCACC AGACGAGTAC TCCAAAACTA ATCG      54

(2) INFORMATION FOR SEQ ID NO:33:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:33:

CCATCAATCG ATCTGGTCAC CGTCTCCTCA GGTCTCTCTA AATAGCAATA TTTACCT      57

(2) INFORMATION FOR SEQ ID NO:34:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:34:

CCATCAATCG ATCTGGTCAC CGTCTCCTCA GGTGGAGGCG GTTCAGGCGG AGGTGGCTCT      60

GGTCTCTCTA AATAGCAATA TTTACCT      87

(2) INFORMATION FOR SEQ ID NO:35:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:35:

```
CATGACCACA GTGCACAGTA ATAATATAAC TTCGTATAAT GTATACTATA CGAAGTTATG    60

CATGCAAATT CTATTTCAAG GAGACAGTC                                      89
```

(2) INFORMATION FOR SEQ ID NO:36:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:36:

```
GTAAAACGAC GGCCAGT                                                   17
```

(2) INFORMATION FOR SEQ ID NO:37:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:37:

```
TTACTGGCGG CCCAGCCGGC CATGGCCGCT CTCTAAATAG CAATATTTAC CTTTGGAG      58
```

(2) INFORMATION FOR SEQ ID NO:38:

(i) SEQUENCE CHARACTERISTICS:
        (A) LENGTH: 82 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:38:

```
CTAATTAAGG GCGGCCGCKN NKNNKNNKNN KNNKNNKNNK NNKNNKNNAT ACCTTACGAG    60

TACTCCAAAA CTAATCAATA TA                                             82
```

(2) INFORMATION FOR SEQ ID NO:39:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:39:

```
TTACTCGCGG CCCAGCCGGC CATGGCCNNK NNKNNKNNKN NKNNKNNKNN KNNKNNKGCT    60

CTCTAAATAG CAATATTTAC CTTTGGAG                                       88
```

(2) INFORMATION FOR SEQ ID NO:40:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:40:

CAGCGTCACC GGAATTCATA CCTTACGAGT ACTCCAAAAC TAATCAATAT A          51

(2) INFORMATION FOR SEQ ID NO:41:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:41:

TCGAGCATAA CTTCGTATAA TATAAACTAT ACGAAGTTAT CGAG          44

(2) INFORMATION FOR SEQ ID NO:42:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:42:

TGCACTCGAT AACTTCGTAT AGTTTATATT ATACGAAGTT ATGC          44

(2) INFORMATION FOR SEQ ID NO:43:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:43:

TCGAGCATAA CTTCGTATAA CATAGCCTAT ACGAAGTTAT CGAG          44

(2) INFORMATION FOR SEQ ID NO:44:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:44:

TGCACTCGAT AACTTCGTAT AGGCTATGTT ATACGAAGTT ATGC          44

(2) INFORMATION FOR SEQ ID NO:45:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:45:

```
GACATGGCCA TGCCATGGCA TGCCGCTCGA GCTCTCTAAA TAGCAATATT TACCTTTGGA      60

G                                                                     61
```

(2) INFORMATION FOR SEQ ID NO:46:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:46:

```
GAGGTCGAAT TCATAAGAAT GCGGCCGCTA AACTATGTGC ACTTACCTTA CGAGTACTCC      60

AAAACTAATC AATATA                                                     76
```

(2) INFORMATION FOR SEQ ID NO:47:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:47:

```
CATGCCGCTC GAGCTCTCTA AATAGCAATA TTTACGTTTG GAG                       43
```

(2) INFORMATION FOR SEQ ID NO:48:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:48:

```
CGAAGGACAA GTGCACTTAC GTTACGAGTA CTCCAAAACT AATCAATATA                50
```

(2) INFORMATION FOR SEQ ID NO:49:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:49:

```
CATGCCGCTC GAGCGGCGGA GGTGGCTCTC TAAATAGCAA TATTTACGTT TGGAG           55
```

(2) INFORMATION FOR SEQ ID NO:50:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:50:

```
CGAAGGACAA GTGCACTACC GCCTCCACCT ACGTTACGAG TACTCCAAAA CTAATCAATA    60

TA                                                                   62
```

(2) INFORMATION FOR SEQ ID NO:51:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:51:

```
GCGATGGTTG TTGTCATTGT CGGC                                           24
```

(2) INFORMATION FOR SEQ ID NO:52:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:52:

```
TTCACAAACG AATGGATCCT CATTAAAGCC AGAATGGAAA GCGCA                    45
```

(2) INFORMATION FOR SEQ ID NO:53:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:53:

```
TTACTCGCGG CCCAGCCGGC CATGGCCGCT CTCTAAATAG CAATATTTAC CTTTGGAG      58
```

(2) INFORMATION FOR SEQ ID NO:54:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:54:

```
TTAAGGAGAG GTCCGACTAT ATCTTA                                         26
```

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:55:

GAAATACCTA TTGCCTACGG                                       20

(2) INFORMATION FOR SEQ ID NO:56:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:56:

GCGTGGTTAG GTCCATGTCC GTCAGC                            26

(2) INFORMATION FOR SEQ ID NO:57:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:57:

GAATTTTCTG TATGAGG                                          17

(2) INFORMATION FOR SEQ ID NO:58:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:58:

TCCTTTAGTT GTTCCTT                                          17

(2) INFORMATION FOR SEQ ID NO:59:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other nucleic acid: Oligonucleotide primer (xi) SEQUENCE DESCRIPTION: SEQ ID NO:59:

ACTTCGTACT GAACGGC                                          17

(2) INFORMATION FOR SEQ ID NO:60:

(i) SEQUENCE CHARACTERISTICS:
        (A) LENGTH: 21 base pairs
        (B) TYPE: nucleic acid (C) STRANDEDNESS: single
            (D) TOPOLOGY: linear (ii) MOLECULE TYPE: Other nucleic acid: Oligonucleotide primer (xi) SEQUENCE DESCRIPTION: SEQ ID NO:60:

GAAGTGATGC AACACTGGAG C                                             21

(2) INFORMATION FOR SEQ ID NO:61:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:61:

Arg His Ser Val
1

(2) INFORMATION FOR SEQ ID NO:62:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:62:

Lys His Ser Val
1

(2) INFORMATION FOR SEQ ID NO:63:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:63:

Arg His Ser Leu
1

(2) INFORMATION FOR SEQ ID NO:64:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:64:

Lys His Ser Leu
1

(2) INFORMATION FOR SEQ ID NO:65:

(i) SEQUENCE CHARACTERISTICS:
            (A) LENGTH: 4 amino acids
            (B) TYPE: amino acid
            (C) STRANDEDNESS: single (D) TOPOLOGY: linear (ii) MOLECULE TYPE: peptide (xi) SEQUENCE DESCRIPTION: SEQ ID NO:65:

Arg His Ser Ile
1

(2) INFORMATION FOR SEQ ID NO:66:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:66:

Lys His Ser Ile
1

(2) INFORMATION FOR SEQ ID NO:67:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:67:

Arg His Ser Xaa
1

(2) INFORMATION FOR SEQ ID NO:68:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:68:

Lys His Ser Xaa
1

(2) INFORMATION FOR SEQ ID NO:69:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:69:

Ser Leu Lys Val Ser Ala Leu
1               5

(2) INFORMATION FOR SEQ ID NO:70:

(i) SEQUENCE CHARACTERISTICS:
            (A) LENGTH: 7 amino acids
            (B) TYPE: amino acid
            (C) STRANDEDNESS: single

```
        (D) TOPOLOGY: linear (ii) MOLECULE TYPE: peptide (xi) SEQUENCE DESCRIPTION: SEQ ID NO:70:

Ser Leu Asn Val Ser Ala Leu
1               5

(2) INFORMATION FOR SEQ ID NO:71:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:71:

Gly Gly Gly Gly Ser Leu Asn Val Gly Gly Gly Gly Ser Ala Leu
1               5                   10                  15
```

RECOMBINANT BINDING PROTEINS AND PEPTIDES

CROSS-REFERENCE TO RELATED APPLICATIONS

This is a continuation of International Application No. PCT/GB94/02662, filed Dec. 5, 1994, and a continuation-in-part of U.S. Ser. No. 08/448,418, filed May 14, 1996, now U.S. Pat. No. 5,837,242, and claims priority for earlier application PCT/GB94/02662.

FIELD OF THE INVENTION

The present invention relates to polypeptides which comprise two or more component polypeptides or peptides, methods for making them and DNA constructs for the use in this making. In particular, it relates to the provision of repertoires of such polypeptides and encoding nucleic acid therefor.

BACKGROUND TO THE INVENTION

In this application, we describe the generation of binding proteins and peptides using nucleic acid containing introns with RNA splice sites such as self-splicing introns, preferably in conjunction with a site-specific recombination system, such as lox P (Hoess et al Proc. Natl. Acad. Sci. USA 79 3398–3402, 1982; Sternberg et al J. Mol. Biol. 150 467–486, 1981). The site-specific recombination allows two sequences of nucleic acid to be cloned separately as libraries and be brought together subsequently by a recombination event (Waterhouse et al Nucleic Acids Res. 21 2265–2266, 1993; A. D. Griffiths et al. EMBO J. in press; WO 92/20791; WO 93/19172. One library of sequence is cloned into a first replicon and a second library of sequences into a second replicon. Recombination between the sites brings together libraries of both sequences on the same replicon. This recombination can be performed in vivo e.g. by P1 infection or by using a recombinase encoded by a plasmid in *E.coli* or in vitro using soluble recombinase. For lox P, the recombinase is Cre. This allows a large library to be made where the limitation is not the cloning efficiency but rather the number of cells which can be grown. Thus the method is particularly powerful in combination with phage display technology which allows the selection of proteins with desired binding properties from a large library of displayed proteins (WO 92/01047; WO 92/20791; WO 93/06213; WO 93/11236; WO 93/19172; WO94/13804). The size of the library is significant for ability to select antibodies or other binding proteins of appropriate affinity and specificity.

WO 93/19172 describes recombining two libraries of nucleic acid using a site-specific e.g. lox P, system mainly to code for heterodimeric proteins in which two chains encoded by distinct (separate) nucleic acid sequences associate to form a functional binding site. Also described is the bringing together of two polypeptides for continuous open reading frames. However, this imposes the use of an amino acid sequence encoded in the site-specific recombination sequence at the junction between the two parts of the sequence, for instance the linker in single chain Fv molecules. A problem with this is that there is only one open reading frame in the lox P sequence and the amino acids encoded by this may be incompatible with the expression of many proteins in functional form. If alternative lox P sites to the wild-type are used (eg see FIG. 4), further different amino acid sequences may be generated, but the possibilities are still restricted.

For instance, functional single chain Fv molecules can be constructed with 15 amino acid linkers encoded in part by the loxP recombination site. The length of the loxP site (34 bp) however means that a minimum of 11 heterologous ("foreign") amino acids must be incorporated into the final expressed protein. This makes the incorporation of a loxP site into a continuous reading frame unsuitable for the construction of a diabody repertoire and also leaves little scope for the modification of scFv linkers to enhance expression.

The present invention involves RNA splicing, particularly the use of self-splicing introns. This allows the recombination site to be inserted within the intron so that amino acids encoded by nucleotides which are spliced out are not incorporated into the final expressed protein. In such circumstances, the only "foreign" amino-acids which need be incorporated are those derived from the sequences at either end of the self-splicing intron. (Note: the amino acid composition and sequence of the product can be engineered with precision and amino acids inserted, substituted or deleted according to choice and using techniques known in the art.)

When a self-splicing intron is used, the amino acids that are incorporated derive from the P1 sequence at the 5' splice site (5'SS) and the P10 sequence at the 3' splice site (3'SS). These pair with the internal guiding sequence of the intron to form hairpin loops (FIG. 1) and splicing then occurs as indicated.

The use of self-splicing introns allows the use of recombination by lox P to be extended to construction of large libraries of contiguous polypeptide chains where the two parts of the chain separated by the intron are varied.

In the application EP 93303614.7, priority from which is claimed by PCT/GB93/02492, an example is given of use of a loxP site inserted within a self-splicing intron with a bivalent or bispecific "diabody". A "diabody" is a multivalent or multispecific multimer (e.g. bivalent or bispecific dimer) of polypeptides wherein each polypeptide in the multimers comprises a first domain comprising a binding portion of an immunoglobulin heavy chain variable region linked to a second domain which comprises a binding protein of an immunoglobulin light chain variable region such that the domain of a given polypeptide cannot associate with each other to form an antigen binding site. Antigen binding sites are formed from an antigen binding site. Antigen binding sites are formed by multimerisation (e.g. dimerisation) of the polypeptides.

The expression of bivalent diabodies from DNA containing a self-splicing intron is shown in FIGS. 1 and 2. Application EP 93303614.7 also shows the use of this system for chain-shuffling. (See also FIG. 3.) WO94/13804 describes splicing out a lox P site using a self-splicing intron for a bispecific diabody (Example 1 of this application). In these two earlier applications the use of self-splicing introns was described for splicing only between the two domains of diabodies. The use of self-splicing introns to bring together two portions of polypeptide chain however has general applicability and can equally well be applied to single chain Fv fragments, peptide libraries or indeed any polypeptide sequence.

The use of systems such as lox P which promote recombination allows one polypeptide sequence to be replaced by another one with a similar or different function, originally encoded on another replicon. This is particularly useful with polypeptide chains such as single chain Fvs which have two or more domains which contribute to function. The invention allows the use of two repertoires of nucleic acid, with a splice site between the two repertoires and proteins or peptides thus encoded selected. In one embodiment, termed "chain shuffling", one nucleic acid sequence is kept constant and the library of other chains recombined at the lox P site in the intron.

Self-splicing introns have been shown to be functional in *E. coli* using a system in which the Tetrahymena intervening sequence (a group I self-splicing intron) was inserted into the gene encoding the α-peptide of β-galactosidase (J. V. Price & T. R. Cech Science 228 719–722, 1985; R. B. Waring et al Cell 40 371–380, 1985; M. D. Been & T. R. Cech Cell 47 207–216, 1986). The presence of blue colonies indicated that self-slicing was functional in *E. coli.*, because the α-peptide complemented the β-galactosidase enzyme acceptor. This system has been used in diagnosis of the intron sequences which are compatible with self-splicing.

Although self-splicing introns have been inserted into functional proteins as above splicing introns have not been used for protein engineering strategies or for processes which involve the recombination of two repertoires of nucleic acid.

SUMMARY OF THE INVENTION

The present invention provides a DNA construct comprising a first sequence of nucleotides encoding a first peptide or polypeptide, a second sequence of nucleotides encoding a second peptide or polypeptide and a third sequence of nucleotides between the first and second sequences encoding a heterologous intron between RNA splice sites and a site-specific recombination sequence within the intron. The presence and position of the RNA splice sites render the intron operable for splicing out of nucleotides from between the first and second sequences upon transcription of the DNA construct into RNA, which may result in splicing together of the first and second sequences. Depending on the intron used, one or more nucleotides may remain between the first and second sequences in transcribed RNA following splicing, resulting in one or more amino acids between the first and second peptides or polypeptides in the product of translation of the RNA. However, those skilled in the art will recognise that the first and second sequences may be termed "exon" sequences.

The term "heterologous" (or "foreign") indicates that the intron is one not found naturally between the first and second sequences in a position operable for removal of nucleotides from between the first and second sequences upon transcription. DNA constructs according to the present invention are "artificial" in the sense that they do not occur naturally, ie without human intervention by means of recombinant DNA technology.

The first and second peptides or polypeptides may be any sequence of amino acids. Preferably, the first and second polypeptides together form a member of a specific binding pair (sbp), such as the antigen binding site of an immunoglobulin (antibody or antibody fragment). Thus, the combination of first and second polypeptides may form a polypeptide sbp member which is a scFv antibody fragment consisting of a VH domain linked to a VL domain by a peptide linker which allows the VH and VL domains of the sbp member to associate with one another to form an antigen binding site. (Bird et al, Science, 242, 423–426, 1988; Huston et al, PNAS USA, 85, 5879–5883, 1988) In such a case, the DNA construct comprises a first sequence of nucleotides encoding a VH or VL domain, a second sequence of nucleotides encoding a counterpart VL or VH domain and a third sequence of nucleotides, between the first and second sequences, comprising a heterologous intron. Upon transcription of the DNA construct into RNA and splicing out of nucleotides of the third sequence, nucleotides of the third sequence remaining in the RNA encode, and are translatable into, the peptide linker of the scFv antibody fragment.

This principle, with nucleotides of the third sequence encoding and being translatable into amino acids of a linker joining the first and second peptides or polypeptide chains, may be used for any peptides or polypeptides, for example in the creation of peptide libraries.

In preferred embodiments of the present invention, the first and second sequences encode peptides or polypeptides which are not linked in any naturally occuring polypeptide. The peptides or polypeptides may be derived from the same naturally occuring molecule but not linked directly by a peptide bond, ie they may be two parts of a polypeptide naturally separated by one or more intervening amino acids. One or both of the first and second peptides or polypeptides may be an antibody fragment, for example VH, VL, CH, CL, VH—CH or VL—CL. The peptide or polypeptide need not be a complete domain. One or both of the first and second peptides or polypeptides may be encoded by a synthetic nucleotide sequence, eg one created randomly. Thus, a random sequence peptide or polypeptide library may be created for example by expression from a repertoire or population of DNA constructs, as disclosed, wherein the first and second exon sequences comprise randomly-generated nucleotide sequences.

The DNA construct may be transcribable into RNA which, following splicing, encodes a "diabody" polypeptide, ie a polypeptide comprising a first domain which comprises a binding region of an immunoglobulin heavy chain variable region and a second domain which comprises a binding region of an immunoglobulin light chain variable region, the domains being linked (eg by a peptide bond or peptide linker) but incapable of associating with each other to form an antigen binding site. Where the domains are linked by a peptide linker, the linker may, for instance, be 10 amino acids or fewer in length. See Holliger et al, PNAS USA 90:6444–6448 (1993) and WO94/13804. Polypeptides of this kind are able to associate with one another to form multivalent or multispecific binding proteins. DNA constructs which can be transcribed into RNA which, following splicing, encodes such a "diabody" polypeptide may, however, be excluded from the present invention.

Other examples of first and second peptides or polypeptides include any polypeptide comprising binding regions of immunoglobulin heavy and light chain variable domains; Vα/Vβ domains of T cell receptors; T cell receptor/antibody (fragment) fusions; peptides, for example for epitope mapping of an antibody, receptor binding peptides, enzyme, eg protease, inhibitors; mutagenesis libraries of any multiple domain protein, for example nucleotide dehydrogenases which have nucleotide binding domains and substrate binding domains, adhesion molecules such as ICAM-1, receptors such as PDGF-receptor which have a ligand binding domain and a kinase domain, transcription factors which have a DNA binding domain and a second domain which interacts with a ligand—such as the glucocorticoid receptor. For a review of multiple domain proteins see Branden and Tooze, "Introduction to Protein Structure", Garland 1991.

The intron may be a self-splicing group I intron such as ICE10 from Tetrahymena (T. R. Cech Ann. Rev. Biochem. 59 543–568, 1990). Splicing out of the intron occurs at the RNA level leaving behind sequences at the 5' and 3' splice sites, which would encode three amino acids between the two peptide or polypeptide components of the product polypeptide. The self-splicing may be designed so that the number of amino acids remaining is different.

Other group I introns or group II self-splicing introns may be used. There are at least 149 self-splicing group I introns known, including: *Tetrahymena thermophila* rRNA intron, *Neurospora crassa* cytochrome b gene intron 1, *Neurospora crassa* mitochondrial RRNA, *Neurospora crassa* cytochrome oxidase subunit 1 gene oxi3 intron, phage T4 thymidylate synthase intron, *Clamydoronas reinhardtrii* 23S rRNA Cr.LSU intron, phage T4 nrdB intron, Anabaena pre tRNA(Leu) intron. Group II self-splicing introns include yeast mitochondrial oxi3 gene intron5γ and *Podospora anserina* cytochrome c oxidase I gene.

Self-splicing introns may be used in combination with recombination, for example, at a lox P site, in the construction of molecules. For example, a lox P site may be included in a self-splicing intron between the two domains (eg VH and VL) of a polypeptide chain. This may, for example, be recombined at the DNA level through a lox P site on another replicon carrying another variable domain gene and the appropriate region of a self-splicing intron. Self-splicing at the RNA level following transcription will now lead to a product polypeptide chain with a new combination of first and second polypeptides.

In one aspect of the present invention the third sequence of nucleotides in the DNA construct, the intron, comprises a sequence for site-specific recombination. The sequence may be suitable for site-specific recombination in vivo and/or in vitro. It may be the lox P site, a 34 bp site at which recombination is catalysed by the protein Cre (Hoess et al., PNAS USA 79:3398–3402, 1982, and Sternberg et al., J. Miol. Biol.; 150:467–480, 1981). The 34 bp of the lox P site consists of two 13 bp inverted repeats separated by an 8 bp non-symmetrical core (see FIG. 4 SEQ. ID NOS:4–9).

In order to provide more controlled recombination between two sequences leading to the resultant recombinant vectors desired, each vector may include two site-specific recombination sequences each of which is different from the other. The sequences should then be such that recombination will take place between like sequences on different vectors but not between the different sequences on the same vector. The use of site-specific recombination allows first and second nucleic acid sequences originally on different (first and second) vectors/replicons to be brought together onto a single recombinant vector/replicon.

Each of the first vectors and each of the second vectors may include a first site-specific recombination sequence and a second site-specific recombination sequence different from the first, site-specific recombination taking place between first site-specific recombination sequences on different vectors and between second site-specific recombination sequences on different vectors but not between a first site-specific recombination sequence and a second site-specific recombination sequence on the same vector.

The first site-specific recombination sequence may be lox P obtainable from coliphage P1 and the second site-specific recombination sequence a mutant lox P sequence, or vice versa. Potentially, both the first and second site-specific recombination sequences may be mutants, as long as the first sequence will not recombine with the each other and second sequences will recombine with each other.

A suitable mutant lox P sequence is lox P 511 (SEQ. ID NO:5). See FIG. 4 SEQ ID NO:4–9.

The first vectors may be phages or phagemids and the second vectors plasmids, or the first vectors may be plasmids and the second vectors phages or phagemids.

This system (ie employing site-specific recombination but not intron splicing) has been used in the preparation of antibodies displayed on phage (P. Waterhouse et al., Nuc. Acid Research 21:2265–2266, 1993; and W093/19172).

In one embodiment, the recombination is intracellular and takes place in a bacterial host which replicates the recombinant vector preferentially over the first vectors and the second vectors. This may be used to enrich selection of successful recombination events. The intracellular recombination may take place in a bacterial host which replicates plasmids preferentially over phages or phagemids, or which replicates phages or phagemids preferentially over plasmids. For instance, the bacterial host may be a PolA strain of *E.coli* or of another gram-negative bacterium. PolA cells are unable to support replication of plasmids, but can support replication of filamentous phage and phagemids (plasmids containing filamentous phage intergenic regions). So, for instance, if the first vectors are plasmids containing a first marker gene, and the second vectors are phage or phagemids containing a second marker gene, selection for both markers will yield recombinant vectors which are the product of a successful recombination event, since recombination transferring the first marker from plasmid must take place in order for that marker to be replicated and expressed.

The bringing together of nucleic acid for two components or subunits of a product polypeptide, initially present on two separate replicons enables favourable combinations of subunit genes to be isolated directly without recourse to extensive recloning, e.g. using phage display. This may be achieved by recombination between the replicons once they have been introduced into the same cell. In a preferred configuration, recombination events are effected such that the genes for one of the component is recombined onto a recipient replicon which contains the gene for a partner component. Preferably, the recipient replicon is capable of being packaged into a bacteriophage particle. Most preferably, the genes encoding one or more of the subunits is fused to a capsid gene such as gIII in order that the functional multimer can be displayed on the surface of the rgdp.

A variety of recombination systems are known, and many of these could be harnessed in such as way as to effect recombination between replicons.

One of the most fully understood site-specific recombination systems is that used in integration and excision of bacteriophage lambda (In "*Escherichia coli* and *Salmonella typhimurium.* Cellular and Molecular Biology." (1987). pp1054–1060. Neidhart, F. C. Editor in Chief. American Society for Microbiology). This bacteriophage can follow two developmental pathways once inside the cell; lysis or lysogeny. The lysogenic pathway involves integration of the lambda genome into the chromosome of the infected bacterium; integration is the result of a site-specific recombination between a ca. 240 bp sequence in the bacteriophage called att P and a 25 bp site in the bacterial chromosome called att B. The integration event is catalysed by a host encoded factor called IHF and a phage encoded enzyme called Int recombinase, which recognises a 15 bp region common to the two att sites. The integrated DNA is flanked by sequences derived from att B and att P, and these are called att L and att R. The integration event is reversible and is catalysed by Int, IHF and a second bacteriophage encoded enzyme, Xis. It is envisaged that this system could be used for sequence transfer between replicons within *E. coli*. For example, the donor gene could be flanked by att L and att R sites such that when Int and Xis proteins are provided in host cell, recombination between att L and att R sites would create a circular DNA segment containing the donor gene and a recreated att B site. This circular segment could then recombine with an att P site engineered into the recipient plasmid.

For the work described in this application, the lox P/Cre system was chosen of the possibilities available because the recombination is highly sequence-specific, very efficient and occurs at a short target site that is readily incorporated into cloning vectors. However, other site-specific recombination systems may be used, for instance: flp recombinase (A. Landy, Curr. Opinion Genetics Devel. 3 699–707, 1993).

A way of enriching for productive recombination events is to employ mutant sites. Several mutants of the lox P sequence are known, and these are compromised with respect to their ability to recombine with each other and the wild-type lox P sequence (Hoess, R. H., Wierzbicki, A. and Abremski, K. (1986) Nucl. Acids Res. 14, 2287–2300). For example, lox P 511 SEQ ID NO:5 has a G->A point mutation in the central 8 bp segment, with the result that it will only recombine with other lox P 511 SEQ ID NO:5 sites, but not the wild-type lox P sequence (Hoess, R. H. Wierzbicki, A. and Abremski, K. (1986) et supra.). Placement of wild-type and mutant lox P sequence combinations can direct which recombination events are possible. The sites loxP1, loxP2, loxP3 and loxP4 (FIG. 4; SEQ ID NOS: 7, 8, 6, & 9, respectively) can be used in a similar way to loxP511 SEQ ID NO:5. These sites do not recombine significantly with loxP511. There is in some cases a degree of recombination between the loxPWT site and these mutant sites, derived from it. For instance, in one experiment 5% recombination was observed between loxP3 SEQ ID NO:6 and loxPWT sites. All of these new loxP sites recombine efficiently with identical sites, ie like sites, eg one loxP4 site with another loxP4 site, and show strong preference for this over recombination with a different site.

Provision of further different mutant loxP sites permits even greater control over the occurrence of recombination events leading to more complex, controllable and efficient recombination strategies being possible. The availability of these loxP sites has allowed the construction of a vector system including 3 loxP sites as in Example 6. This 3loxP system offers two additional features compared with the systems containing two loxP sites:

(a) It should facilitate chain shuffling of light and heavy chain genes for affinity maturation of antibody fragments (see Marks et al (1992), Bio/Technology 10, 779–783) since one variable domain may be kept constant and a library of VH and VL genes recombined with it using an appropriate donor vector.

For example, a clone specific for an antigen may be isolated where the gene for a VH domain of a scFv fragment is located between loxP511 and loxp wt SEQ ID NO:4 of a vector containing 3 loxP sites, such as fd3lox. A library of VL domains may then be shuffled with the VH domain gene kept constant by recombining the clon in the 3 loxP site vector with a library of VL genes on a donor vector such as pUC19 which are located between the loxP4 site and the loxp 511 SEQ ID NO:5 site. The library of VL domain genes is now encoded in the 3 lox site vector and scFv fragments, eg with improved affinity, may be selected from the phage displayed scFv fragment repertoire.

Although chain shuffling may be performed in 2 loxP systems, this 3loxP system gives more flexibility, particularly to the nature of the replicon, phage or plasmid, where the reshuffled repertoire is expressed, since both repertoires are flanked by loxP sites.

Example 6 and FIG. 13 show the use of a loxP system in model experiments for the construction of a diabody or single chain Fv repertoire where the VH and VL genes are separated by a self-splicing intron containing a loxP site. The design of the system will faciliate chain shuffling as above.

(b) It facilitates the transfer of light and heavy chain gene pairs which have been selected on the surface of filamentous bacteriophage for binding to antigen into a soluble expression vector for expression of e.g. soluble-scFv fragments, which at present needs to be done by cloning using restriction enzymes. The transfer by recombination could be achieved by creating an expression vector containing a new mutant loxP site such as loxP4 SEQ ID NO:9 and the WT SEQ ID NO:4 site and by recombination between these two sites and the corresponding sites on the fd3lox vector. Model experiments for this are described in example 6 and FIG. 13.

The use of three different loxP sites also allows, for example, the recombination of three sequences in order. One sequence to be recombined could be flanked by loxP and loxP511 SEQ ID NO:5, a second sequence by loxP511 SEQ ID NO:5 and loxP3 SEQ ID NO:6. These sequences may then be recombined into a third replicon containing a third DNA sequence and three loxP sites. The location of 2 loxP sites within different self splicing introns allows the three sequences to be expressed continuously as shown in FIGS. 7 and 8.

Selection of productive arrangements may be facilitated by use of a polA strain of bacteria, preferably *E. coli* or other gram negative bacterium. These cells are deficient in DNA polymerase I and are unable to support replication of plasmids (Johnston, S. and R, D. S. 1984, supra.). However, they are able to support replication of filamentous phage and plasmids containing filamentous phage intergenic regions. If Cre-catalysed recombination is performed in polA bacteria, by selecting for the presence of both selectable markers in the same polA cell successful recombination events are enriched, since recombination must take place for the second marker gene to be replicated and expressed. The resulting cells then contain the complete repertoire and can be propagated as cells and infected with helper phage to produced phagemids containing the genes for both chains and expressing them on their surface.

The invention also provides a vector comprising a DNA construct as disclosed. Generally, the vector comprises nucleic acid necessary for expression. The vector may comprise nucleic acid for secretion of the product polypeptide upon expression.

The present invention also provides a method of producing a polypeptide product which comprises a combination of a first peptide or polypeptide component and a second peptide or polypeptide component, the method comprising:

providing a DNA construct comprising a first sequence of nucleotides encoding a first peptide or polypeptide, a second sequence of nucleotides encoding a second peptide or polypeptide and a third sequence of nucleotides between the first and second sequences encoding a heterologous intron with a site-specific recombination sequence within the intron;

transcribing DNA of the construct into RNA;

causing or allowing splicing of nucleotides of the third sequence to produce an RNA molecule encoding the polypeptide product;

translating the RNA molecule into the polypeptide product.

The transcription, splicing and translation steps may take place in in vitro or in vivo systems. Conveniently, and particularly preferably for the construction of repertoires, these steps are performed in vivo, eg in *E. coli*. Splicing may also be accomplished, less preferably, using in introns which are not self-splicing, by introducing the components of the splicing apparatus of eukaryotic cells, which promote splicing (J. A. Wise Science 262 1978–1979, 1993; A. J. Lamond, BioEssays 15 595–603, 1993), into eg *E. coli*.

The DNA construct provided may be any as discussed above. Suitable vectors for expression (transcription) can be chosen or constructed, containing appropriate regulatory sequences, including promoter sequences, terminator fragments, polyadenylation sequences, enhancer sequences, marker genes and other sequences as appropriate, as is well known to those skilled in the art. For further details see, for example, Molecular Cloning: a Laboratory Manual: 2nd edition, Sambrook et al, 1989, Cold Spring Harbor Laboratory Press. Transformation procedures depend on the host used, but are well known.

Preferably, a phage or phagemid vector is used and the vector, with the DNA construct, packaged into a bacteriophage particle. Advantageously, the polypeptide product comprises a domain which is a surface component of an organism such as a bacteriophage, for example a filamentous bacteriophage such as fd or M13. Preferably, the surface component is GIII of bacteriophage fd or the equivalent from another filamentous 'phage. Suitable technology is described in WO92/01047, WO92/20791, WO93/06213, WO93/11236, WO93/19172 and PCT/GB93/02492. Thus, the provided DNA construct is packaged into a particle which displays on its surface the polypeptide product of expression from the construct, including the splicing step. In this way, polypeptide product with binding affinity or enzymatic eg catalytic affinity for a target can be extracted from medium or selected from a mixture of different polypeptide products without such binding affinity or enzymatic activity, by contact with target eg using a chromatographic technique. Where the polypeptide product is a sbp member, selection may be on the basis of binding affinity for complementary sbp member: eg an immunoglobulin binding domain (such as scfv fragment) can be selected on the basis of binding affinity for antigen.

The step of provision of a DNA construct may actually involve the provision of a plurality, eg a repertoire, of constructs with different nucleic acid sequences. The term "repertoire" is used to indicate genetic diversity, ie variety in nucleotide sequence, and generally implies a large number of different sequences, perhaps of the order of millions (eg $10^7$-$10^9$-$10^{12}$-$10^{14}$). Highly diverse repertoires may be created when a sequence for site-specific recombination, (as discussed, eg lox P wild-type or mutant), is included within the third sequence in the DNA construct at a site compatible with splicing upon transcription. The size of a library generated by recombination between one library and another is limited only by the transfection efficiency. In principle, if each library contains, $10^7$ clones, each recombination may introduce a further level of diversity of $10^7$, thus recombination between a first repertoire encoding $10^7$ different VH domains with a second repertoire encoding $10^7$ different VL domains yields a recombinant repertoire encoding $10^{14}$ different product polypeptides. Similarly, two libraries of $10^3$ clones can be recombined to give a library of $10^6$ clones.

For example, a first repertoire of replicons comprising nucleic acid encoding a repertoire of first peptide or polypeptide component may contain part of a self-splicing intron, while a second repertoire of replicons comprising nucleic acid encoding a repertoire of second peptide or polypeptide component contains a complement part of the self-splicing intron. The replicons in each of the first and second repertoires of replicons each comprise a sequence for site-specific recombination, suitably positioned such that recombination of a replicon from the first repertoire of replicons with a replicon from the second repertoire of replicons results in formation of the self-splicing intron in the resultant recombinant replicon. Alternatively, replicons in either or both of the first and second repertoires may contain a complete self-splicing intron.

The first and second repertoires of replicons may be recombined ("crossed"), eg at a site-specific recombination sequence, to produce a third repertoire of (recombinant) replicons which includes nucleic acid encoding a plurality of different combinations of first and second peptide or polypeptide component, with a self-splicing intron between the nucleic acid encoding the first and second peptide or polypeptide components on each replicon. The recombination may take place in vivo in bacterial host cells following transfection with the first repertoire of replicons and subsequent transfection with the second repertoire of replicons. If the sequences for site-specific recombination are lox P, the recombination may be catalysed by Cre recombinase.

Transcription of nucleic acid in the third repertoire of replicons into RNA is followed by splicing out of the intron containing the sequence for site-specific recombination, leaving mRNA coding for polypeptide product which can be translated into the polypeptide product. The production of a repertoire of polypeptide products comprising different combinations of first and second peptide or polypeptide components may be followed by a step of selection of products of interest, such as those with a particular binding specificity or enzymatic activity.

Each replicon in the third repertoire of replicons may comprise a sequence enabling packaging of the replicon into a bacteriophage particle, and the polypeptide product may comprise a surface component of a bacteriophage, as discussed. Then, particles may be selected from a repertoire of particles by their display of polypeptide product with a binding specificity or enzymatic activity of interest. Each selected particle then contains DNA encoding that polypeptide product.

FIG. 5 demonstrates the principle for use in production of a scFv repertoire. There the "first polypeptide component" of the polypeptide product is a VH domain (SEQ ID NO:13) and the "second polypeptide component" of the polypeptide product is a VL domain (SEQ ID NO:11). A lox P site is included within a Class I self-splicing intron. The peptide linker of each scfv fragment in the product repertoire is formed, at least in part, by remnants of the splice sites left after splicing out of the intron between the VH SEQ ID NO:13 and VL SEQ ID NO:11 domains upon transcription.

Instead of using two repertoires in the generation of a recombinant repertoire for expression, a single first or second peptide or polypeptide component may be "chain shuffled" against a repertoire of corresponding second or first peptide or polypeptide component. Thus, in the generation of a repertoire of scFv fragments to be used in selection for a scFv fragment able to bind to an antigen of interest, either a VH or a VL domain known to be able (with complementary VL or VH domain) to bind to the antigen may be combined with a repertoire of complementary VL or VH domain to produce a repertoire for expression followed by selection on the antigen for pairings able to bind.

A further aspect of the present invention provides nucleic acid comprising a sequence of nucleotides encoding self-splicing intron with a site-specific recombination sequence, such as a loxP site or a mutant or derivative thereof, within the intron. Preferably such nucleic acid consists essentially of a sequence of nucleotides encoding self-splicing intron with a site-specific recombination sequence within the intron. Such nucleic acid may be isolated and is suitable for use in creation of constructs for use in a method as herein disclosed. Preferably, the nucleic acid comprises restriction sites flanking the intron, for ligation of nucleic acid encoding or peptides. The nucleic acid may be incorporated in a vector operably linked, ie under the control of, a promoter for expression. Other preferred features are as disclosed herein with reference to the methods and the DNA constructs. In particular, the site-specific recombination sequence within the intron is preferably heterologous, as discussed.

SELF-SPLICING TO FORM DIABODIES OR SINGLE CHAIN Fv FRAGMENTS

A recombination site (eg. lox P) may be included in a self-splicing intron between the two antibody domains of the polypeptide chain. This may, for example, be recombined at the DNA level through a lox P site on another replicon carrying another variable domain gene and the appropriate region of a self-splicing intron. Self-splicing at the RNA level following transcription will now lead to a diabody polypeptide chain with a new combination of variable domains or a single chain Fv polypeptide, depending on the length of the linker region encoded. In WO 94/13804 the splicing of an intron from RNA encoding a diabody polypeptide is described. This can readily be extended to single chain Fv fragments by introducing the sequence encoding the extra amino acids on either side of the RNA splice sites encoding the appropriate length of linker.

Chain shuffling can be performed for bivalent or bispecific diabodies or for single chain Fv fragments using the systems described in FIGS. 3 and 5. As noted above, a further level of control may be established by the use of a system with 3 loxP sites, as shown in FIG. 13. The expression of diabody and single chain Fv molecules from clones containing loxP sites within self splicing introns is demonstrated in examples 1, 2 and 4. Example 3 demonstrates the feasibility of making a large library which recombines two exons into a longer continuous sequence. This methodology for making a repertoire can be applied to other molecules such as single chain Fv fragments and diabodies where the VH and VL genes replace the peptide sequences. Example 6 describes model experiments which demonstrate that recombination can be performed between loxP sites configured for the construction of diabody or single chain Fv repertoires. It is concluded that this methodology is suitable for the libraries described in example 3 and Griffiths et al (1994, supra) and that libraries of more than $10^{12}$ independent scFv or diabody clones are feasible.

As discussed further herein, introns with splice sites, such as self-splicing introns, containing an internal lox P site may be applied to any other system where two functional domains come together, for instance T cell receptors or two domain proteins. In addition to proteins with natural variants such as antibodies, for any two domain proteins mutagenesis libraries can be made for the two domains and then combined using the lox P system.

In addition to splicing together libraries of domains, such as VH and VL domains, parts of domains may be spliced together, eg using a self-splicing intron. For instance, the use of a self-splicing intron containing a recombination site such as lox P in framework 3 of V domains allows recombination of fragments containing CDRs 1 and 2 with fragments containing CDR3, eg in CDR3 shuffling.

SPLICING INTRONS/RECOMBINATION IN THE CONSTRUCTION OF PEPTIDE LIBRARIES

Libraries may be made where two sequence encoding peptides are encoded separated by a self-splicing intron containing a recombination, eg lox P, site. For instance, two separate libraries of ten amino acid peptides can be cloned and then recombined via the lox P 511 SEQ ID NO:5 and lox P sites as is shown in FIG. 6. The amino acids encoded by the region of the 5' and 3' splice sites make this into a total 25 amino acid peptide with 5 constant amino acids in the center. The peptide library can then be used for a number of purposes, for instance the epitope mapping of antibody binding sites or to derive new molecules such as receptor binding proteins, protease inhibitors or substrates.

Example 3 shows that a large phage display library of ca. $5 \times 10^{10}$ recombined 25 amino acid peptides may be constructed using recombination between loxP sites contained in a self splicing intron and peptides containing the epitope recognised by an anti-p53 antibody selected. Constrained peptide libraries may be made by incorporating a cysteine residue in each of the 10 amino acid peptides to be recombined so that a disulphide bond is formed and the peptides between the cysteine would form a loop. The five amino acid linker may be varied in length and amino acid sequence by varying the 5' and 3' splice sites and the reading frame. The number of random amino acids may also be varied and need not be the same on either side of the linker. This example demonstrates the feasibility of making a large library which recombines two exons into a longer continuous sequence.

USE OF TWO OR MORE INTRONS IN CONSTRUCTION OF RECOMBINANT ANTIBODIES

Two or more splicing introns may be used to link together three or more nucleic acid sequences encoding polypeptides. This may be particularly advantageous in constructing libraries where V—D—J recombination (for the antibody heavy chain) occurs in *E. coli*. The use of site-specific recombination sequences (e.g. lox P) within the introns (e.g. using the scheme in FIG. 7) allows this V—D—J recombination of VH domains to occur in *E. coli* in the presence of recombinase (Cre for lox P). The VH, DH and JH regions may be natural V, D and J genomic segments regions or derived from synthetic oligonucleotide sequences, perhaps of different lengths, especially for the D region, so that the range of CDR3 lenghts generated by the recombination may reflect the same (or a modified) distribution of natural CDR3 lengths and the presence or absence of N base addition. FIG. 7 shows the use of lox P to achieve V—D—J recombination to obtain a single chain Fv molecule and FIG. 8 shows the expression of this molecule. The introns and splice donor and acceptor sites need to be designed to ensure that splicing does not cut out the exon sited between the two introns. The introduction of a fourth intron containing a different recombination site would allow the linking of different CH1 domains to the J region.

An analogous system may be used for T cell receptors a similar system may be used for reshuffling V and J regions of light chains.

SELECTION OF SEQUENCES FOR THE 5' AND 3' SPLICE SITES

When an intron is deleted by a self-splicing process, a residue of the intron is left behind within the coding region of the polypeptide, due to the 5' and 3' splice sites. Example 1 shows two different amino acid sequences incorporated into a diabody due to this residue of the intron, with variation in expression occurring. There are likely to be differences in the expression of a number of proteins depending on the nature of the P1 and P10 sequences. Therefore, there may be a need in certain cases to identify amino acids which are compatible with successful splicing of the intron and expression of protein.

Identification of suitable amino acids incorporated due to the bases at the 5' and 3' splice sites may be done by mutating bases (eg randomly) in the region of the internal guiding sequence with complementary bases which form the Pi hairpin loop of the intron. If the intron is now inserted, between the nucleic acid encoding the first and second peptides or polypeptides, for instance between the VH and VL domains of antibody fragment, such that efficiently spliced polypeptide product is produced and may be displayed on phage and selected by binding to target, those sequences compatible with efficient splicing can be selected. Similarly, sequences of the 3' splice site can be varied together with those of the internal guiding sequence and those which are efficiently spliced selected by the expression of the polypeptide sequence.

The above procedures apply when the bases of the internal guiding sequence that are to be changed only participate in one of the P1 and P10 hairpin loops It can be seen from FIG. 1 that the central bases of the internal guiding sequences participate in both the P1 and P10 hairpin loops. Thus for these bases it is necessary to mutate the bases of both the 5' and 3' splice sites as well as the internal guiding sequence in order to maintain complementarily and self splicing.

Example 4 shows that mutations may be made at the 3' splice site and internal guiding sequence of the self splicing intron to allow the encoding of amino-acids compatible with higher expression, after self splicing of RNA, of both diabody and single chain Fv antibody fragments. This directed mutation procedure may be applicable to other sites of the self splicing intron.

When repertoires are to be made, the GLSSG SEQ ID NO:16 sequence (SEQ ID NO:16) used in Example 1 may be used as the first trial sequence for the sequence linking the two polypeptides following splicing out of the intron. Further sequences identified, eg using a mutation process as described in Example 4, may be used as alternatives.

To select the sequences of the splice site at the 5' end of the exon which are retained in the mature protein after splicing of the pre-mRNA that are compatible with self-splicing, the sequences of known self-splicing introns may be examined (F. Michel and E. Westhof J. Mol. Biol. 216 581–606, 1990; F. Lisacek et al J. Mol. Biol. 235 1206–1217, 1994). Sequences compatible with self-splicing leading to the incorporation of favourable amino acids may then be chosen.

CONTROL OF SELF-SPLICING USING STREPTOMYCIN

Streptomycin prevents self-splicing. Thus the use of streptomycin in Str-R *E. coli* will prevent splicing occurring in transcribed RNA. The removal of streptomycin will aloow the generation of a spliced RNA product, leading to, on translation, a protein product which is only generated on splicing. Thus, one could have a cloned gene which does not express an active protein in the presence of streptomycin in the growth medium, but does so in its absence. This may be useful for expressing proteins which are toxic or reduce growth in *E. coli* for example antibodies directed against *E. coli* proteins or inhibitors of *E. coli* enzymes, where expression of the toxic protein can be switched off until required.

The present invention will now be illustrated further by way of example. Modifications and variations within the scope of the present invention will be apparent to those skilled in the art.

All documents mentioned in the text are incorporated herein by reference.

FIG. 1 shows a schematic of a self-splicing intron, including the P1 and P10 helices and the internal guiding sequence. The splice sites are marked by arrows.

FIGS. 2(*a*)–(*c*) illustrates the expression of a single chain Fv or diabody from DNA (FIG. 2*a*) containing a self splicing intron. The transcribed DNA (FIG. 2*b*) is self spliced to produce RNA lacking the Lox P 511 site (FIG. 2*c*).

FIGS. 3(*a*)–(*f*) illustrates chain shuffling of a diabody (or a single chain Fv) molecule. It shows the replicons generated by Cre-mediated recombination between the acceptor phage vector fdDOG-2dialoxsplice (A) and the donor plasmid vector pUC19-2dialoxsplice (B). A is based on fd-tet-DOG1, with the chain VHA-VLB in one cistron under control of the gene III promoter. Between VHA and VLB is inserted the self-splicing intron from Tetrahymena containing the lox P 511 recombination site inserted at a site compatible with self-splicing activity. B is based on pUC19 and contains lox P 511, the distal part of the self-splicing intron from Terahymena, VLA, and the lox P wild type sequence in the same arrangement as A. Within *E. coli* an equilibrium between the six replicons develops due to the reversible nature of recombination in th lox-Cre system. The same scheme will apply to both single chain Fv and diabody molecules, depending on the length of the linker peptide between the variable domains. Product E would express fd phage displaying a single chain Fv or a diabody depending on the linker length used.

A and B can cointegrate by recombination between either mutant or wild-type loxP sites to create chimaeric plasmids C and D respectively. Further recombination can then occur between the two wild-type or the two mutant loxP sites, to generate the original vectors (A and B) or two new vectors (E and F). The light chains of A and B are therefore exchanged, and product E now encodes fd phage displaying a single chain Fv or a diabody depending on the linker length used. Product F contains the VL originally in A. Within *E. coli* an equilibrium between the six replicons develops due to the reversibel nature of recombination in the lox-Cre system.

FIG. 4 shows the sequence of wild type (SEQ ID NO:4) and mutant (SEQ ID NO:5–9) lox P sites.

FIG. 5 illustrates the generation of a single chain Fv SEQ ID NO:15 repertoire by recombination between repertoires of VH SEQ ID NO:13 and VL SEQ ID NO:11 domains.

Figure 3:
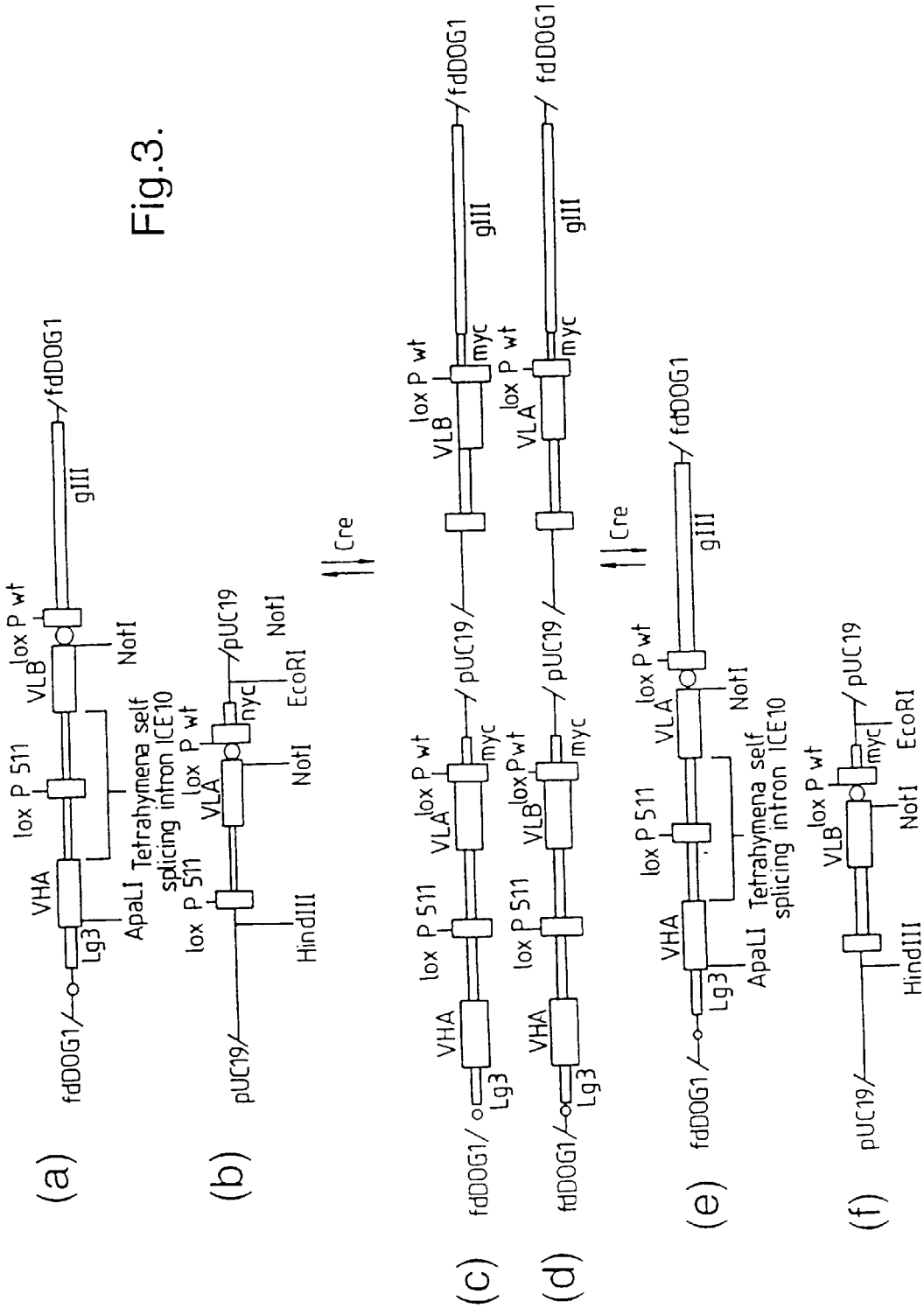
Figure 6:
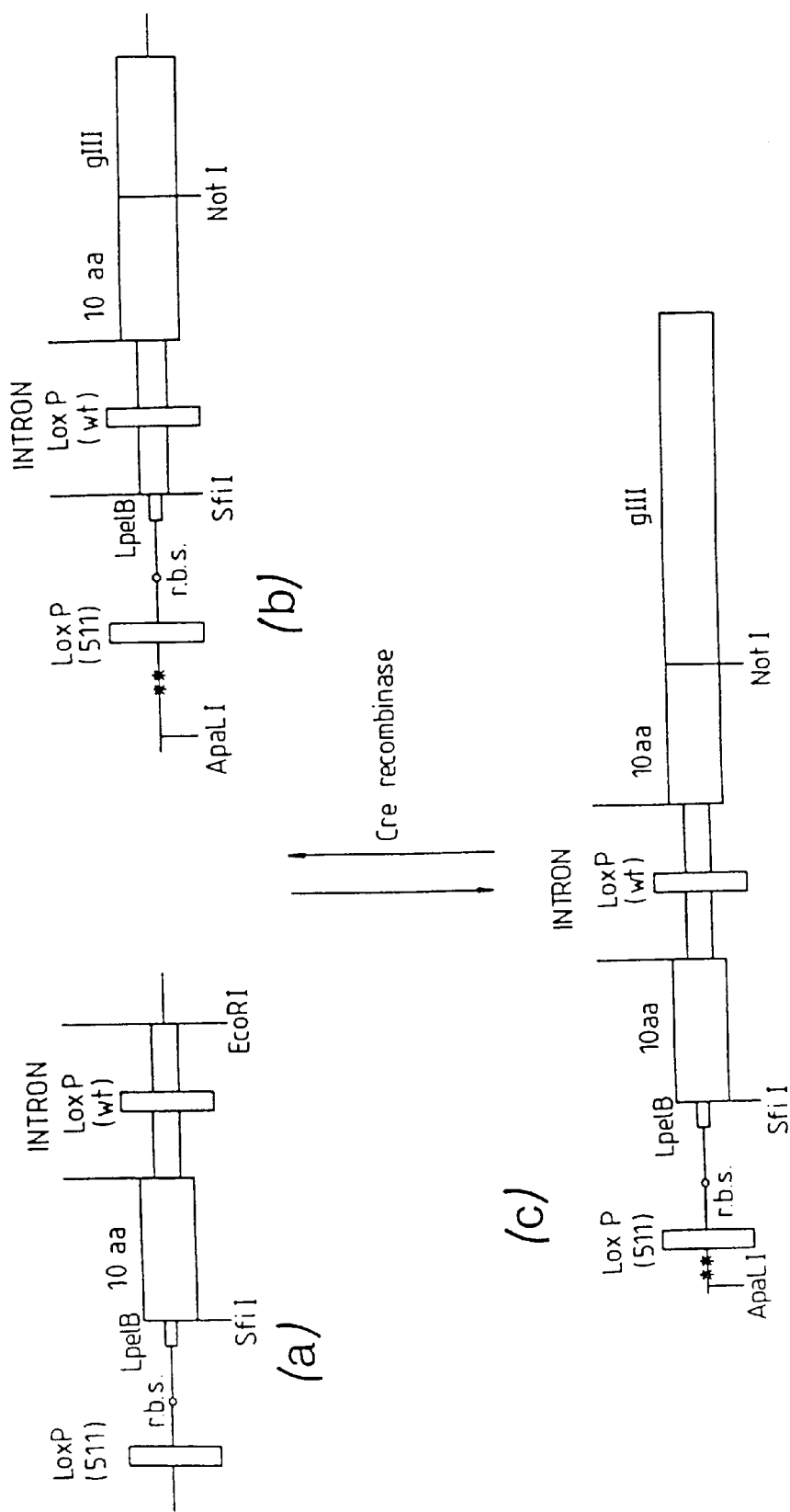

FIGS. 6(*a*)–(*c*) illustrates the generation of a peptide library by recombination between two replicons (a) pUC19-PEP and (b) fdDOG-PEP to produce the product (c) rbs represents ribosome binding sites; LpelB is the leader peptide sequence; gIII is fd phage gene III; 10aa is a random oligonucleotide (NNK)$_{10}$ encoding ten amino acid residues (K is an equimolar mixture of G and T); * is an ochre stop codon. The expressed sequence (SEQ ID NO:17) is: aa1—aa2—aa3—aa4—aa5—aa6—aa7—aa8—aa9—aa10—A—L—L—R—Y—aa11—aa12—aa13—aa14—aa15—aa16—aa17—aa18—aa19—aa20.

FIGS. 7(*a*)–(*d*) illustrates the recombination of V, D and J regions using recombination between lox P sites within self splicing introns. The VH, DH and JH regions may be natural VH, DH and JH regions or derived from synthetic oligonucleotides sequences, perhaps of different lengths, especially for the D region, so that the range of CDR3 lengths generated by the recombination, reflects the same (or a modified) distribution of natural CDR3 lengths. The scheme is shown for a single chain Fv molecule with the VL domain fused to gene III protein. lx1, lx2 and lx3 are 3 different lox P sites e.g. wild type lox P, lox P511 and lox P3(SEQ ID NO:6). in2 and in3 are the two introns which contain lx2 and lx3 sites such as the Tetrahymena rRNA and the T4 sunY intron. (a) Acceptor vector; (b) donor vector 1; (c) donor vector 2; (d) recombined fd phage.

FIGS. 8(a)–(d) shows the transcription, splicing and expression of a single chain Fv molecule constructed as in FIG. 7, containing recombined V, D and J regions, fused to gene III protein. The nucleic acid regions encoding the amino acids of the final product are shown as Expressed scFv-gene III fusion. (a) DNA; (b) Primary transcript; (c) Spliced transcript; (d) Expressed scFv-geneIII fusion.

FIG. 9 shows an alternative final product from recombination which mimics VH, DH and JH recombination in vitro to generate a new VH domain. Two separate libraries of sequences of random nucleotides (x and y) which encode 0 to 15 amino acids are made and recombined using the lox/Cre system. lx1 and lx2 are two distinct lox sites such as lox P5 511 and lox P (wild type). This scheme requires only one self-splicing intron and two different lox P sequences.

FIGS. 10(a)–(d) show the construction of the vector fdDOG-PEP. (a) pUC19 NQ10K; (b) fd DOG-FCK; (c) INTRON_LoxP(wt); (d) fd DOG-PEP; r.b.s.—ribosome binding sites; LpelB—leader peptide sequence; gIII—fd phage gene III (gIII); 10 aa—random oligonucleotide; *—OCHRE stop codon.

FIGS. 11(a)–(d) show the construction of the vector pUC19-PEP. (a) pUC19 NQ10 K; (b) fd DOG-BLX; (c) INTRON_LoxP(wt); (d) fd DOG-PEP; r.b.s.—ribosome binding sites; LpelB—leader peptide sequence; gIII—fd phage gene III (gIII); 10 aa—random oligonucleotide; *—OCHRE stop codon.

FIGS. 12(a)–(d) show construct fdDWT/3 and three different linkers formed on expression from constructs described in example 4. Sequence A (SEQ ID NO:19) is derived from the unmutated self splicing intron. Sequence B (SEQ ID NO:21) is derived from the self splicing intron mutated at the 3' splice site and in the internal guiding sequence. Sequence C (SEQ ID NO:23) shows the sequence derived from the single chain Fv fragment. Bases contributing to the P1 and P10 hairpin loops are underlined. Restriction site bases are outlined. The diagonal slashed line shows the bases between which the self-splicing intron is spliced out. T7 is the promoter for T7 RNA polymerase. Fx is a site for Factor X protease. Part D shows the schematic of the self splicing intron highlighting the bases which are mutated (G to C in the P10 hairpin loop and its complementary base in the internal guiding sequence).

FIG. 13a shows the fd phage acceptor vector, fdDWT/4 containing 3 lox sites is shown. It contains the VH and VL genes of the anti-NIP clone G6 (Griffiths et al, 1994 supra). The sites loxP511 and loxPWT SEQ ID NO:4 flank the VH gene and the sites loxPWT and loxP4 SEQ ID NO:9 flank the VL gene. The loxPWT site is in the self splicing intron and the loxP4 site sits between the VL gene and gene III. The diabody or single chain Fv polypeptide chain encoded is expressed as a fusion with the gene III protein. A site for the factor X protease is included between the VL gene and gene III to allow the possibility of the elution by proteolysis of phage from the antigen during selection procedures. Alternative versions of fdDWT/4 were also made with the site loxP4 replaced with loxP3 SEQ ID NO:6 and loxP1 SEQ ID NO:7 respectively. The donor vector PDN8 contains the VH-D10 gene flanked by loxP511 and loxPWT sites. The donor vector pRWT/4 contains the VL-D10 gene flanked by loxPWT SEQ ID NO:4 and loxP4 sites. In the donor vectors pRWT/3 or pWT/1 the loxP4 SEQ ID NO:9 site of pRWT/4 is replaced by the loxP3 SEQ ID NO:6 or loxP1 SEQ ID NO:7 site respectively. The expression vector pEX511/4 contains the S12 gene, which confers streptomycin sensitivity on bacteria, flanked by loxP511 and loxP4 sites.

FIG. 13B summarises the recombination efficiencies obtained in the experiments described in example 6. The left hand loxP site is loxP511, the middle loxP site is the loxP site within the self splicing intron and the right hand loxP site is the loxP site between the VL gene and gene III.

DETAILED DESCRIPTION

EXAMPLE 1

USE OF SELF-SPLICING INTRONS IN THE CONSTRUCTION OF DIABODY MOLECULES

In the work described in this example, a self splicing intron was introduced between the VH and VL domain genes of two antibodies cloned in the diabody format, NQ11 and D1.3 directed against 2-phenyloxazol-5-one and hen egg lysozyme respectively. This self splicing intron was shown to be spliced out following expression, as determined by the expression of functional bivalent diabodies.

Construction of NQ11 and D1.3 clones containing a self-splicing intron, excised to leave a five amino acid linker between VH and VL domains of bivalent diabodies The self-splicing intron from Tetrahymena (T. R. Cech Ann. Rev. Biochem. 59 543–568, 1990) has been shown to be able to splice in the E. coli cytoplasm. Such a self-splicing intron, from clone ICElO (Ian Eperon, University of Leicester) was inserted between the genes encoding the VH and VL domains of the antibodies D1.3 and NQ11 in such a way as to create upon splicing out an open reading frame encoding a diabody with linker (SEQ ID NO:16) VH-GLSSG-VL. Without splicing no functional diabody can be produced as the self splicing intron contains several stop codons in 3 reading frames.

A restriction site for BstEII was incorporated at the 5' end of the primer T1baBstEII (SEQ ID NO:33) and a SacI restriction site introduced in the primer T1foSac. This allowed the self splicing intron fragment to be cloned in a 2-way ligation reaction into the expression vectors pUC119D1.3 (encoding the V domains of the D1.3 anti-lysozyme antibody) or pUC19NQ11 (encoding the V domains of the anti-phox antibody NQ11) each cut with BstEII and SacI.

T1baBstEII SEQ ID NO 33 primes at the 5' end of the self splicing intron and conserves the internal guidance sequence (IGS) required for splicing activity and inserts a extra glycine residue at the 3' end of the VH domain. T1foSac primes at the 3' end of the self splicing intron and conserves the thymidine base just 3' of the self splicing intron which, though not part of the intron, is present in Tetrahymena DNA. TlfoSac inserts a extra Gly and Ser residue at the 5' end of the VL creating a 5 amino acid linker.

The self splicing intron was amplified with the primers T1baBstEII (SEQ ID NO:33) and T1foSacI (SEQ ID NO:32) using standard conditions (see eg example 14 of PCT/GB93/02492). The product of the PCR reaction was digested with restriction enzymes SacI and BstEII and ligated into BstEII/SacI digested pUC119D1.3 or pUC19NQ11 in a molar ratio 4:1 (SSI:pUC119D1.3 or pUC19NQ11) and the resulting ligation mixes used to transform E. coli TG1 cells. Recombinants were screened for inserts of correct size using primers specific for self splicing intron, T1foSac and T1baBstEII.

Soluble diabody was expressed by growth at 37° C. Cells in log phase growth in 2 mL 2YT/0.1% glucose/100 µg mL$^{-1}$ ampicillin were induced by adding IPTG to a final concentration of 1mM IPTG and grown 3 hours 22° C. The cells were centrifuged (1000 g 10 minutes) and the cell pellet resuspended in 100 µl ice cold PBS/1mM EDTA and left on ice, 60 minutes. The cell suspension was centrifuged (1000 g for 10 minutes) and the diabody-containing supernatant used in ELISA on lysozyme and phOx (as described in example 1 of PCT/GB93/02492).

The ELISA signal (absorbance at 405 nm) was equivalent (greater than 1.0 after 10 min) for the spliced 5 amino acid linker D1.3 diabody to that obtained with the 5 amino acid linker D1.3 diabody (constructed in example 1 of PCT/GB93/02492). However for the spliced 5 amino acid linker NQ11 diabody the signal was much lower (0.2 compared to 2.0 after 20 min) when compared to the 5 amino acid linker diabody constructed in example 1 of PCT/GB93/02492. There three possible explanations for this:

the NQ11 diabody is not functional with the GLSSG SEQ ID NO 16 linker sequence (SEQ ID NO:16), although this appears unlikely;

self-splicing does not work properly in the case of the diabody NQ11 because the DNA sequence 3' of the intron (at the 5' of the VL domain) is not suitable for self splicing. Whereas the D1.3 sequence at 5' end of the VL domain gene is efficient at allowing self splicing, the NQ11 sequence in this region is poor;

there is a cryptic splice site in this construct.

Construction of NQ11 and D1.3 clones containing a self-splicing intron including a loxP site, excised to leave a six amino acid linker between VH and VL domains of bivalent diabodies The primers T1ba2BstEII and T1fo2SacI were designed to introduce into the NQ11 construct sequences 3' of the self splicing intron which should enable efficient self splicing at the RNA level.

The self splicing intron was amplified with T1ba2BstEII and T1fo2SacI by PCR. This intron was inserted between the VH and VL domain genes of antibody NQ11 and creates upon splicing out an open reading frame encoding a diabody with linker (SEQ ID NO:28) VH-GSLKVG-VL. Without splicing no functional diabody can be produced as the self splicing intron contains several stop codons in 3 reading frames.

A restriction site for BstEII was incorporated at the 5' end of the primer T1ba2BstEII SEQ ID NO 33 and a SacI restriction site introduced in the primer T1fo2Sac.(SEQ ID NO:30). This allowed the self splicing intron fragment to be cloned in a 2-way ligation reaction into the expression vector pUC19NQ11 cut with BstEII and SacI. T1ba2BstEII primes at the 5' end of the self splicing intron and conserves the bases at the 5' splice site which pairs with the internal guidance sequence (IGS) required for splicing activity and inserts a extra glycine residue at the 3' end of the VH. T1fo2Sac primes at the 3' end of the self splicing intron and conserves the thymidine base just 3' of the self splicing intron which, though not part of the intron, is present in Tetrahymena DNA and inserts a extra Gly and Ser residue at the N-terminal end of the VL domain.

The self splicing intron used in this case contained a lox P site inserted between bp 236 and 237. It was amplified with the primers T1ba2BstEII and T1fo2SacI using standard conditions. The product of the PCR reaction was digested with restriction enzymes SacI and BstEII and ligated into BstEII/SacI digested pUC19NQ11 in a molar ratio 4:1 (SSI:pUC19NQ11) and the resulting ligation mix used to transform *E. coli* TG1 cells.

Recombinants were screened for inserts of correct size using the primers specific for self splicing intron, T1fo2Sac and T1ba2BstEII SEQ ID NO 33.

Soluble diabody was expressed as above and assayed by ELISA. In this case an equivalent signal (greater than 1.0 after 10 min) was obtained with the 6 amino acid linker NQ11 diabody formed by self splicing as for the 5 amino acid linker diabody constructed in example 1 of PCT/GB93/02492. Thus this strategy allows more efficient self splicing in the NQ11 construct.

EXAMPLE 2

USE OF SELF-SPLICING INTRONS IN THE CONSTRUCTION OF A SINGLE CHAIN FV CLONE

In the work described in this example, a self-splicing intron is introduced between the VH and VL domain genes of an antibody, D1.3, cloned in the single chain Fv format, directed against hen egg lysozyme. This self-splicing intron is shown to be spliced out following transcription, as determined by the expression of a functional single chain Fv molecule with a 15 amino acid linker.

Construction of D1.3 clone containing a self-splicing intron, excised to leave a fifteen amino acid linker between VH and VL domains of a single chain Fv molecule The self-splicing intron from Tetrahiymena (T. R. Cech Ann. Rev. Biochem. 59 543–568, (1990)) has been shown to be able to splice in the *E. coli* cytoplasm. It is inserted between the genes encoding the VH and VL domains of the antibody D1.3 in such a way as to create upon splicing out an open reading frame encoding a scFv with linker (SEQ ID NO:29) VH-GGGGSGGGGSGLSSG-VL. Without splicing no functional scFv can be produced as the self-splicing intron contains several stop codons in three reading frames.

A restriction site for BstEII is incorporated at the 5' end of the primer T1bascEvBstEII (SEQ ID NO:34) and a SacI restriction site is introduced in the primer T1foSac. This allows the self-splicing intron fragment to be cloned in a 2-way ligation reaction into the expression vector pUC119D1.3 (encoding the V domains of the D1.3 anti-lysozyme antibody: Holliger et al (1993) supra) each cut with BstEII and SacI.

T1bascFvBstEII SEQ ID NO 34 primes at the 5' end of the self-splicing intron and conserves the sequences at the 5' splice site which pair with the internal guidance sequence (IGS) required for splicing activity, and inserts an extra 10 amino acid residues at the 3' end of the VH. T1foSac primes at the 3' end of the self-splicing intron which, though not part of the intron, is present in Tetrahymena DNA and inserts extra serine and glycine residues at the N-terminal end of the VL domain.

The self-splicing intron used in this case contained a lox P site inserted between bp 236 and 237. It was amplified with the primers T1bascFvBstEII (SEQ ID NO:34) and T1foSacI using standard conditions. The product of the PCR reaction was digested with restriction enzymes SacI and BstEII and ligated into BstEII/SacI digested pUC119D1.3 in a molar ratio 4:1 (SSI:pUC119D1.3) and the resulting ligation mix used to transform *E. coli* TG1 cells. Recombinants were screened for inserts of correct size using the self-splicing intron specific primers T1foSac and T1bascFvBstEII.

Soluble single chain Fv is expressed as in example 1 and assayed for ability to bind lysozyme by ELISA. A signal of greateer than 1.0 is obtained after 10 minutes. Hence, self-splicing introns may be used in nucleic acid encoding single chain Fv molecules.

EXAMPLE 3

CONSTRUCTION OF A DIVERSE REPERTOIRE OF 25 AMINO ACID PEPTIDES (CONTAINING 20 VARIED RESIDUES) DISPLAYED ON PHAGE USING LOX P RECOMBINATION SITES WITHIN SELF SPLICING INTRONS

In the work described this example a diverse repertoire of 25 amino acid peptides (consisting of two variable 10 amino acid peptide sequences separated by five constant amino acids) displayed on bacteriophage was prepared by the recombination of two separate repertoires of 10 amino acid peptides cloned in separate replicons. Recombination between the lox P sites under the control of the Cre recombinase allows their sequences to be linked. The final repertoire thus prepared combines the diversity of the two peptide libraries (FIG. 6).

Construction of the vector fdDOG-PEP

The VHCH fragment of the antibody NQ10/12.5 was amplified from the vector pUC19 NQ10 k using oligo 3249 (SEQ ID NO:35), which introduces the lox P 511 site upstream of the pelB leader sequence and an ApaLI restriction site (see Table 1 and FIG. 10) and oligo LMB2 (SEQ ID NO:36). The resulting fragment was then cloned into fdDOG1. (T. Clackson et al, supra) cut with ApALI and NotI. The group I self-splicing intron from Tetrahymena (T. R. Cech et al Structural Biology 1 273–280, 1994) containing a wild type lox P site (between nucleotide 236 and 237) was amplified with oligo 3189 (SEQ ID NO:53) (which introduces a EcoRI restriction site) and oligo 3190 (SEQ ID NO:38) (which includes the random oligonucleotide $(NNK)_{10}$ and a NotI restriction site). The resulting fragment was then cloned into fdDOG-BLX cut with SfiI and NotI to create the vector fdDOG-PEP.

Construction of the vector DUC19-PEP

The group I self-splicing intron from Tetrahymena containing a wild type lox P site (between nucleotide 236 and 237) was amplified with oligo 3194 (SEQ ID NO:39) (which introduces a EcoRI restriction site and includes the random nucleotide $(NNK)_{10}$ (Table 1, FIG. 11) and oligo 3198 (SEQ ID NO:40 (which introduces a SfiI restriction site. The resulting fragment was then cloned into pUC19-21ox (P. Waterhouse et al, 1993 supra) cut with SfiI and EcoRI to create the vector pUC19-PEP (FIG. 11).

Combinatorial infection and in vivo recombination

To create a large combinatorial repertoire of 25 amino acid peptides (with 20 amino acids displayed varied) on a fd phage the strategy of combinatorial infection and in vivo recombination was used (P. Waterhouse et al Nucleic Acids Res. 21. 2265–2266, 1993). This system uses the lox-Cre site-specific recombination system to bring the two 10 amino acid repertoires together on the same replicon, separated by a self-splicing intron.

$10^9$ E. coli TG1, harbouring the library of 10 amino acid peptides in fdDOGPEP was used to inoculate 1 liter of 2xTY broth containing 12.5 $\mu$g/ml tetracycline (2xTY-TET) and the culture shaken for 30 hours at 30° C. in two 500 ml aliquots in 2 liter baffled Erlenmayer flasks. Phage were purified from the supernatant by precipitation with polyethylene glycol (J. McCafferty et al, Nature 348 552–554, 1990), resuspended in PBS (phosphate buffered saline (phosphate buffered saline: 25mM $NaH_2PO_4$, 125mM NACl, pH7.0). Phage were titred by infecting exponential phase E. coli TG1 (30 min, 37° C.) and plating on TYE-TET. Yields are typically $6 \times 10^{13}$ t.u. per liter of culture.

$2.4 \times 10^8$ E. coli harbouring the plasmid pACYCara/Cre (Example 5) and the library of 10 amino acid peptides cloned in pUC19 PEP were used to inoculate 200 ml of 2xTY containing 100 $\mu$g/ml carbenicillin, 25 $\mu$g/ml chloramphenicol, 2g/l glycerol and 1% glucose (2xTYCaChglyglc) and grown overnight at 37° C. with shaking. 10 ml aliquots of the overnight culture were used to inoculate 10×1 liter culture of 2xTYCaChglyglc in 21 Erlenmeyer baffle flask and the culture grown with shaking at 37° C. to $A_{600}$ of 0.4.

$1.4 \times 10^{12}$ t.u. of fdDOG PEP library were added to each Erlenmeyer baffle flask and incubated for 10 mins at 37° C. without shaking. The 2xTYCaChglyglc containing the infected cells were then filtered through a 0.45 $\mu$m tangential flow filter (PELLICON cassette, MILLIPORE), and resuspended in 10×1 liter 2xTY containing 100 $\mu$g/ml carbenicillin, 25 $\mu$g/ml chloramphenicol, 15 $\mu$g/ml tetracyclin, 2g/l glycerol and 0.5 g/l L(+) arabinose (2xTYCaChTetglyara) in 2 liter Erlenmeyer baffle flasks and the culture grown with shaking at 30° C. for 36 hrs. A sample was taken before growth to determine the library size by plating on 2xTY agar plates containing carbenicillin, chloramphenicol and tetracyclin. There were $4.7 \times 10^{10}$ independent clones.

The culture was then filtered as before. The recombined phage, in the filtrate, were precipitated using PEG/NaCl and resuspended in a final volume of 26 ml PBS. The phage were titred by infecting exponential phase E. coli (30 mins, 37° C.) and by plating on TYE-tet. The yield obtained was $6.0 \times 10^{13}$ t.u. total (the fdDOG-REC library glycerol stock). To determine the frequency of recombination, a PCR screen was performed by amplifying DNA from individual colonies using oligos 4226 and pelBBACK (Table 1; SEQ ID NOS:56 & 55, respectively, ). 13 clones out of 50 screened gave a band on electrophoresis on a 6% polyacrylamide gel whose mobility corresponds to a size of 314 base pairs (the expected size from recombined phage) and the others a band whose mobility corresponds to a size of 284 base pairs (the expected size from unrecombined phage). The recombination frequency was thus 26%. As there are multiple copies of plasmid and phage replicons in each bacterial cell when Cre recombinase is induced to promote recombination, and at least 60 phage are produced per bacterium after overnight growth, we believe that each bacterium should yield at least one phage containing the peptide from the donor vector and that the overall library size is $4.7 \times 10^{10}$ clones.

Propagation of phage from the recombined library 10 liters of 2xTY-TET were inoculated with a 35 ml aliquot of the recombined fdDOG-REC library glycerol stock ($2.4 \times 10^{11}$ c.f.u). The cultures were grown with shaking overnight at 30° C. in baffled flasks (1 liter medium per flask). The cultures were centrifuged at 5000 g for 15 min at 4° C., the fd phage precipitated from the supernatant using polyethylene glycol and each repertoire resuspended in a final volume of 10 ml PBS. Total phage yields (from 10 liters) are typically around $10^{14}$ t.u.

In vitro splicing of the intron within the recombined phage

To test for the splicing of the intron within the recombined phage, 5 clones out of 31 positive recombined clones were amplified using oligo-3520 and fdSEQ1 SEQ ID NO:57). The size of the product after PCR was 619 base pairs (expected size for a recombined phage) and 589 base pairs (expected size for a unrecombined phage). The in vitro transcription was performed on 5 clones using an in vitro transcription kit (Promega, Riboprobe II core System T7 RNA Polymerase, cat.#P2590) according to the manufacturer's instructions (1 unrecombined and 4 recombined). The samples were boiled and electrophoresed on a 6% polyacrylamide gel.

All 4 recombined clones showed a band corresponding to the spliced exon (198 bp); and the unrecombined one gave a band whose mobility corresponds to 168 bp (spliced exon). These results indicate that the splicing reaction occurs in the unrecombined phage as well as in the recombined one.

Selection of clones from the library

The peptide library displayed on phage was selected for the ability to bind an anti-p53 antibody (Pab240) which recognize a linear epitope on the surface of the cell with the amino acid sequence RHSV (C. W. Stephen & D. P. Lane J. Mol. Biol 1992 225 577–583).

The selection was performed on Immunotubes (Nunc; Maxisorp) coated with the anti-p53 antibody coated at 10 μg/ml using methodology as previously described (J. D. Marks et al., J. Mol. Biol., 222, 581–597. 1991; A. D. Griffiths et al., (1993) EMBO J., 12, 725–734). Four rounds of growth and selection were performed for binding of peptides displayed on phage to the anti-p53 antibody on Immunotubes using methodology as described by A. D. Griffiths et al (1994) EMBO J., 13 3245–3260). The ability of phage from single isolated clones to bind to anti-p53 antibody was assessed by ELISA on plates coated with antibody p53. Phage were prepared as described by McCafferty et al (supra) and ELISA was performed as described by Griffiths et al, (1993 supra) except that the second antibody used was an anti-sheep antibody coupled to alkaline phosphatase.

31 clones giving positive ELISA signals were amplified by PCR using oligo 3870 (SEQ ID NO:58) and fd SEQ1 (SEQ ID NO:57) (Table 1). Aliquots were analysed by electrophoresis on a 1% agarose gel. The remaining product was purified using Magic PCR Preps (Promega) and used in PCR cycle sequencing reactions with fluorescent dideoxy chain terminators (Applied Biosystem) and oligos 4445 (SEQ ID NO:59) and 3358 according to the manufacturer's instructions. The sequences are shown on table 1.

To check that the selected clones were specified, the same phage from single isolated clones were assayed by ELISA for binding to antibodies with the same isotype as Pab240 (IgG1) and either lambda and kappa light chains (Fog-1 and Fog-B). The ELISAs showed that none of the selected clones cross-reacted with these antibodies.

It was concluded that the same epitope RHSV (SEQ ID NO:61) is selected as a consensus sequence selected from the phage peptide library as described by Steven & Lane (1992, supra). Of the 31 selected peptides displayed on phage, 8 included the sequence RHSV (SEQ ID NO:61), 4 KHSV (SEQ ID NO:62) and 5 (R or K)HS(L or I) (SEQ ID NOS:63–66) and 3 (R or K)HSX (SEQ ID NOS:67&68).

Thus a large phage display library of ca. $5 \times 10^{10}$ recombined 25 amino acid peptides may be constructed using recombination between loxP sites contained in a self splicing intron. This method should be particularly valuable for selecting, for example, peptides involved in binding to receptors. Constrained peptide libraries could be made by incorporating a cysteine residue in each of the 10 amino acid peptides to be recombined so that a disulphide bond is formed and the peptides between the cysteine would form a loop. The amino acid linker could be varied in length and amino acids by varying the 5' and 3' splice sites and the reading frame.

This example demonstrates the feasibility of making a large library which recombines two exons into a longer continuous sequence. This methodology for making a repertoire may be applied to other molecules, including, for example, single chain Fv fragments and diabodies.

EXAMPLE 4
MUTATION OF THE 3' SPLICE AND INTERNAL GUIDING SEQUENCE OF A SELF SPLICING INTRON CONTAINING A LOXP SITE TO ENCODE A NEW DIABODY LINKER WHICH IS COMPATIBLE WITH HIGHER EXPRESSION.

To utilise recombination by loxP in the construction of antibody repertoires a loxP site can be included between the two antibody domains, VH and VL of a single chain Fv fragment, in a continuous open reading frame, employing the amino acid sequences encoded by those loxP sequences as a linker. In this case the choice of linker is dictated by the length and sequence of the loxP sites used. An alternative strategy is to employ RNA splicing of a group I self splicing intron inserted between the VH and VL. A recombination site such as loxP may be inserted within the intron so that the amino acid sequence encoded by the site is spliced out from the RNA after expression and is therefore not incorporated into the final expressed protein.

When a group I intron is deleted by self-splicing process, a residue of the intron, derived from the 5' and 3' splice sites (which pair with the internal guiding sequence in the P1 and P10 hairpin loops respectively), remains within the coding region of the polypeptide. Successful splicing is dependent on base pairing in the P1 and P10 hairpin loops involving the internal guiding sequence (IGS).

This example demonstrates that the 3' splice site and the internal guiding sequence may be mutated so that following splicing the amino acids encoded by the RNA are altered. These amino acids contribute to a 7 amino acid (diabody) linker which is compatible with higher level expression. It is further shown that the mutated 3'splice site can be used in the construction of a single chain Fv molecule containing a 15 amino acid linker. In this example, vectors encoding scFv fragments or diabodies directed against the hapten NIP (3-iodo-4-hydroxy-5-nitrophenyl-acetate) are constructed and expressed using self splicing introns which include loxPWT sites to link the VH and VL domains.

1. Construction and expression of anti-NIP diabody from an expression vector containing loxP in a self splicing intron, and mutation of the P10 hairpin loop.

A diabody expression vector containing loxP in its self splicing intron is shown in FIG. 12. Salient features of the construction of this vector are given below. The intron was amplified by PCR from the vector pUS19Tet-intron-loxP (which contains the loxPWT sequence inserted between bp236–237 of the Tetrahymena ICE10 intron sequence) using #3312 intron-lox-back (SEQ ID NO:45) and 3463 intron-for-2 (SEQ ID NO:46) oligos (Table 1) which contain the sequences of the 5' splice site and the internal guiding sequence of the p1 hairpin loop flanked by a XhoI and NcoI sites at the 5' end, and 3' splice site of the P10 hairpin loop flanked by an ApaLI site and NotI at the 3' end respectively. The amplified product was cloned as a NcoI-EcoRI fragment into pUC19-21ox (Waterhouse et al, 1993 supra). The intron is flanked by XhoI and ApaLI sites.

For the experiments described in this example, the VH and VL genes originate from the Fab fragment clone G6 (anti-NIP; A.D. Griffiths et al EMBO J. 13 3245–3250, 1994). The VH gene was cloned into the pUC vector derivative as a NcoI-XhoI fragment. Promoter sequences for T7 RNA polymerase were introduced into the HindIII site and were flanked by SalI and HindIII sites. The salI-NotI fragment containing the VH-NIP, self-splicing intron, loxP sites and T7 polymerase promoter was now subcloned from the pUC vector derivative into fd-DOG1 (Clackson et al Nature 352 624–628, 1991) which had its ApaLI site converted to a SalI site. The VL gene of G6 was cloned in as a ApaLI-NotI fragment. An AscI site was subsequently introduced at the 3' end of the VL gene with a loxP3 site and a Factor X protease cleavage site between this AscI site and a NotI site at the 5' end of gene III. The resulting construct fdDWT/3 is shown in FIG. 12.

After splicing the RNA transcribed from fdDWT/3 encodes the polypeptide chain of an anti-NIP diabody with a seven amino acid linker SLKVSAL (SEQ ID NO:69) (FIG. 12a). TG1 cells were transformed with fdDNA encoding the construct and phage were prepared as described in A. D. Griffiths et al (1994, supra). This diabody was poorly expressed. The phage titer was lower than $10^7$ TU/ml (at least a hundred fold lower than would be normally expected). There was no detectable signal in the phage ELISA for binding to NIP-BSA performed as described by Griffiths et al. (1994, supra). However, the intron was shown to be spliced correctly as shown by sequencing of the cDNA made from the spliced transcript.

To test for intron splicing the vector was first amplified by PCR with the primers fd-PCR-Back (SEQ ID NO:51) and BamHI-for (SEQ ID NO:52) to prepare the DNA template containing the T7 promoter sequence (Table 1). From this template RNA was prepared using an in vitro transcription kit (Promega, Riboprobe II core System T7 RNA Polymerase, cat.#P2590). The original DNA template was first removed by digestion with DNaseI, and cDNA was then prepared using the First-Strand cDNA Synthesis Kit (Amersham). The cDNA was amplified by PCR with VH3BackSfi and JK-FOR primers (J. D. Marks et al, J. Mol. Biol.222 581–597, 1991), and was sequenced using the same primers.. The sequence obtained demonstrated accurate splicing resulting in an SLKVSAL linker (SEQ ID NO:69) in the expressed diabody product.

To improve expression, amino acids more compatible as linkers for the expression of diabody may be identified and used to alter the bases of the splice sites. To this end a second anti NIP diabody was constructed in which the first G within the 3' splicing signal (P10) was mutated to C SEQ ID NO:27. To enable perfect pairing with the IGS the corresponding C within the IGS was changed to G SEQ ID NO:25 (FIG. 12d). The intron of the vector pUC19Tet-intron-loxP was amplified by PCR with a second set of primers, #3877 (SEQ ID NO.47) encoding P1 and the mutated C to G in the IGS, and #3878 (SEQ ID NO:48) encoding P10 having a G to C mutation (Table 1). The intron was cloned as above to give an analogous fdDWT/3 construct, but in this case after splicing of the intron, the resulting RNA encodes the linker (SEQ ID NO:70) VH-SLNVSAL-VL (FIG. 12b). The splicing of the mutated intron was tested by the cDNA sequencing of expressed RNA as above.

The mutation of K to N in the diabody linker dramatically improved the expression of the diabody, displayed on phage fd, resulting in a phage titer in the range of $5\times10^8$–$10^9$TU/ml and a phage ELISA signal for binding to NIP-BSA in the range of 1 absorbance unit.

Since diabodies require two polypeptide chains to form the antigen binding site (P. Holliger et al 1993, supra) and the only diabody polypeptide chains present are fused to gene III-protein, the ELISA signal indicated that some diabody polypeptide chains are cleaved from the fusion and combine with the gIII-diabody polypeptide fusion retained on the surface of the phage, to form a functional bivalent diabody which can bind to a NIP. Western blots were performed of phage proteins with detection with an antibody directed against gene 3 protein as described by J. McCafferty et al (Protein Engineering 4 955–961, 1991). This gave the relative proportions of gIII protein-diabody polypeptide fusion to cleaved fusion migrating at the position of native gIII protein to be 40% and 60%, respectively.

2. Expression of anti-NIP scFv from an expression vector containing loxP in a self splicing intron, and a mutation of the P10 hairpin loop.

Since the SLNVSAL linker (SEQ ID NO:70), derived by splicing of the mutated P10 hairpin loop, was compatible with the (high) expression of a diabody, a single chain Fv construct was made with a 15 amino acid linker which utilises the same mutated P10 hairpin loop for the self-splicing intron. The self-splicing intron containing the loxP site is spliced out to give the amino acid sequence GGGGSLNVGGGGSAL (SEQ ID NO:71) (FIG. 12c).

The self splicing intron was amplified by PCR from the vector pUC19Tet-intron-loxP using the oligonucleotides 4243 (SEQ ID NO:49) and 4244 (SEQ ID NO:50) (Table 1). These contain bases encoding a stretch of four glycine residues flanking the 5' and 3' splice sites respectively. Oligonucleotide 4243 (SEQ ID NO:49) contains the mutation of the internal guiding sequence and oligonucleotide 4244 (SEQ ID NO:50) and the mutation of the 3' splice site, to effect the K to N mutation as above. The intron is spliced out after transcription and there is functional display of anti-NIP scFv fragments on the surface of phage fd as determined by phage ELISA on NIP-BSA with an absorbance of 1.0. Further, the phage titre was in the range of $5\times10^8$–$1\times10^9$TU/ml, indicating that these phage fd clones grew well.

Thus, mutations may be made at the 3' splice site and internal guiding sequence of the self splicing intron to allow the encoding of amino acids compatible with higher expression on self-splicing. Depending on the amino acid which it is desired to alter, it may be necessary to mutate the bases of the P1 hairpin loop as well as the P10 hairpin loop or the P1 hairpin loop only.

EXAMPLE 5
CONSTRUCTION OF THE PLASMID pACYCaraCre EXPRESSING CRE RECOMBINASE UNDER THE CONTROL OF AN ARABINOSE PROMOTER In the work described in this example, a plasmid was constructed in which Cre recombinase is expressed under the control of a promoter inducible by arabinose. The origin used p15A makes it suitable for use in combination with plasmids with ColE1 origin and with phage or phagemids with phage origins.

A fragment was amplified by PCR from pUC119 (Vieira, J. and Messing, J. (1987). Methods in Enzymol. 153, 3–11) using the primers lacfor2 and lacback2. This fragment extended from within the lacI gene fragment (inactive) to the polylinker of pUC119 and the primers incorporate a series of restriction sites at both ends of the fragment.

This PCR fragment was cut with PvuII and KasI and re-cloned into pUC119 digested with the same enzymes to generate pUC119lacipoly.

pARA14 (Cagnon, C., Valverde, V. and Masson, J. M. (1991). Protein Engineering 4, 843–847) was digested with SacI and NcoI to release a fragment containing the araC gene and the promoter-operator region of araB. This fragment was ligated into pUC119lacipoly cut with the same enzymes to generate pUC119ara.

The Cre recombinase gene was amplified by PCR from bacteriophage P1Cm cl.100 r⁻m⁻ (Yarmolinsky, M. B., Hansen, E. B., Jafri, S. and Chattoraj, D. K. (1989). J. Bacteriol., 171, 4785–4791) using the primers crefor and creback. After digestion with BsaI and KpnI this fragment was ligated into pUC119ara cut with NcoI and KpnI to generate pUC119araCre.

Finally, the PvuII-HindIII fragment of pUC119araCre containing the araC gene and the Cre recombinase gene under the control of the promoter-operator region of arab was subcloned into pACYC184 (Chang, A. C. Y. and Cohen, S. N. (1978). J. Bacteriol., 134, 1141–1156) cut with BsaBI and HindIII, thereby replacing the tetracycline resistance gene of pACYC184. The plasmid produced (pACYCaraCre) thus contains the an arabinose inducible Cre gene on a plasmid with a p15A origin of replication. This plasmid can co-exist in E. coli with both the heavy chain donor vector (which has a ColE1 origin) and with the acceptor vector (which has a filamentous phage origin) and is useful for the generation of a large phage display library in the lox P format.

EXAMPLE 6
MODEL EXPERIMENTS FOR THE CONSTRUCTION OF A DIABODY REPERTOIRE USING THE FD3LOX SYSTEM, USING A LOXP SITE WITHIN A SELF-SPLICING INTRON

In this example, model experiments are described which demonstrate that the loxP site within the self-splicing intron may be used in the construction of a diabody or single chain Fv repertoire by recombination of VH and VL gene repertoires. To this end model experiments are described using a fd phage acceptor vector containing 3 lox sites encoding an anti-NIP diabody molecule, where recombination is performed with donor vectors encoding VH or VL domains. Recombination of the diabody cassette with an expression vector is also demonstrated. The methods of this example are equally applicable to the construction of single chain Fv repertoires using 15 amino acid linkers as described in Example 4, and other polypeptides.

The fd phage acceptor vector, fdDWT/4 containing 3 lox sites is shown in FIG. 13. It contains the VH and VL genes of the anti-NIP clone G6 (Griffiths et al, 1994 supra). The sites loxP511 SEQ ID NO:5 and loxPWT SEQ ID NO:4 flank the VH gene and the sites loxPWT and loxP4 SEQ ID NO:9 flank the VL gene. The loxPWT site is in the self splicing intron and the loxP4 site sits between the VL gene and gene III. The diabody or single chain Fv polypeptide chain encoded is expressed as a fusion with the gene III protein. A site for the factor X protease is included between the VL gene and gene III to allow the possibility of the elution by proteolysis of phage from antigen during selection procedures. Alternative versions of fdDWT/4 were also made with the site loxP4 replaced with loxP3 SEQ ID NO:6 and loxP1 SEQ ID NO:7 respectively (see FIG. 12).

If, for example, a VL gene repertoire is first cloned into fdDWT/4 as ApaLI-AscI fragments, a VH gene repertoire may then be introduced by recombination with a donor vector containing the VH gene repertoire, flanked by loxP511 SEQ ID NO:5 and loxPWT sites.

fSeWT/4 was recombine d with the donor vector pDN8 containing the VH-D10 gene flanked by loxP511 and loxPWT sites. This was performed by transforming E. coli TGl pACYCaraCre (Example 5) with pND8 donor vector containing VH-D10 and then infecting with fdWT/4 phage containing the genes encoding the variable domains, VH-GG and VL-GG. Recombination was allowed to continue at 30° C. overnight. Recombined phage from the bacterial supernatant were used to infect TG-1. As a result of recombination between the loxP511 sites of donor and acceptor and between the loxPWT sites of the donor and acceptor, the recombined fd phage contains VH-D10 while keeping the original VL-G6.

Successful recombination was analysed by PCR screening of individual fd phage clone colonies by amplification using oligonucleotides that prime specifically on the sequences encoding the VL-G6 and VH-D10 CDR3s present in the donor vectors. Thus a PCR product is only observed when recombination has occurred. The recombination efficiency was 75%. Similar experiments recombining fdDWT/3 or fdDWT/1 with pDN8 gave similar efficiencies (FIG. 13).

Alternatively, a VH gene repertoire may be cloned between the NcoI and XhoI sites of fdWT/4 and a VL repertoire, flanked by loxPWT SEQ ID NO:4 and loxP4 SEQ ID NO:9 sites.

fdDWT/4 was recombined with the donor vector pRWT/4 containing the VL-D10 gene flanked by loxPWT and loxP4 sites. This was performed by transforming TG1 pACYCara-Cre (Example 5) with pRWT/4 donor vector containing VL-D10 and then infecting with fdDWT/4 phage containing the genes encoding the variable domains, VH-G6 and VL-G6. Recombination was allowed to continue at 30° C. overnight. Recombined phage from the bacterial supernatant were used to infect TG-1. As a result of recombination between the loxP4 SEQ ID NO:9 sites of donor and acceptor and between the loxPWT SEQ ID NO:4 sites of the donor and acceptor, the recombined fd phage contains VL-D10 while keeping the original VH-G6.

Successful recombination was analysed by PCR screening of individual fd phage clone colonies by amplification using oligonucleotides that prime specifically on the sequences encoding the VH-G6 and VL-D10 CDR3s present in the donor vectors. Thus a PCR product is only observed when recombination has occurred. The recombination efficiency was less than 10%. Similar experiments recombining fdDWT/3 or fdDWT/1 with the donor vectors pRWT/3 or pWT/1 (where the loxP4 site of pRWT/4 is replaced by the loxP3 SEQ ID NO:6 or loxP1 SEQ ID NO:7 site respectively) gave efficiencies of 0% and 96% respectively.

Since in fdDWT/4 the diabody polypeptide is only made as a fusion with gene III, phage displayed bivalent diabody results from the association of free diabody polypeptide, cleaved from gene III protein, with diabody polypeptide gene III fusion. It is desirable to express the bivalent diabody directly as a soluble molecule.

To test the feasibility of subcloning directly into an expression vector by recombination using the loxP sites, the expression vector pEX511/4 was constructed (FIG. 13). This contains the S12 gene, which confers streptomycin sensitivity on bacteria, flanked by loxP511 SEQ ID NO:5 and loxP4 SEQ ID NO:9 sites. E. coli TG1 pACYCaraCre (Example 5) were transformed with pEX511/4 and then infected with fdDST/4 containing the genes encoding the variable domains, VH-G6 and VL-G6.

Recombination is allowed to continue at 30° C. overnight and the cells were replica plated on 2xYT agar with or without streptomycin. If recombination has occurred the genes encoding the diabody polypeptide will have replaced the streptomycin sensitivity gene in pEX511/4. This will make the bacteria streptomycin resistant.

The recombination was shown to have taken place with an efficiency of 40 to 70%. Similar experiments were performed where fdDWT/3 or fdWT/1 were recombined with pEX511/3 or pEX511/1 (where the loxP4 SEQ ID NO:9 site of pEX511/3 was replaced with the loxP3 SEQ ID NO:6 or loxP1 SEQ ID NO:7 site respectively). No recombination was observed.

Thus it is demonstrated that recombination can be performed between loxP sites configured for the construction of diabody or single chain Fv repertoires.

A preferred approach to construction of a repertoire may be first to clone the VL genes as ApaLI-AscI fragments into fdDWT/4 and then recombine with a VH repertoire as NcoI-XhoI fragments in pDN8. This would generate a diabody repertoire (or single chain Fv repertoire, if modified slightly) suitable for phage display. Following selection of diabodies, individual or pooled clones could be subcloned into pEX511/4 for soluble expression. In conjunction with the results from the peptide display chain Fv expression from clones containing self-splicing introns with loxP sites in examples 1, 2 and 4, it is concluded that this methodology is suitable for making large diabody and single chain Fv repertoires of the order of $10^{10}$ to $10^{12}$ or more independent clones.

TABLE 1

Oligonucleotides

| | |
|---|---|
| T1fo2Sac | 5'-GAG CCA TCA ATC TCG GAG CTC GAT GTC ACC TAC CTT ACG AGT ACT CCA AAA CTA ATC A-3' |
| T1ba2BstE | 5'-CCA TCA ATC GAT CTG GTC ACC GTC TCC TCA GGC TCT CTA AAT AGC AAT ATT TAC CT-3' |
| T1foSacI: | 5'-GAG CCA TCA ATC TCG GAG CTC GAT GTC ACC AGA CGA GTA CTC CAA AAC TAA TCG-3' |
| T1baBstEII | 5'-CCA TCA ATC GAT CTG GTC ACC GTC TCC TCA GGT CTC TCT AAA TAG CAA TAT TTA CCT-3' |
| T1bascFvBstEII | 5'-CCA TCA ATC GAT CTG GTC ACC GTC TCC TCA GGT GGA GGC GGT TCA GGC GGA GGT GGC TCT GGT CTC TCT AAA TAG CAA TAT TTA CCT-3' |
| Oligo 3249 | 5'-CAT GAC CAC AGT GCA CAG TAA TAA TAT AAC TTC GTA TAA TGT ATA CTA TAC GAA GTT ATG CAT GCA AAT TCT ATT TCA AGG AGA CAG TC - 3' |
| LMB 2 | 5'-GTA AAA CGA CGG CCA GT - 3' |
| Oligo 3189 | 5'-TTA CTG GCG GCC CAG CCG GCC ATG GCC GCT CTC TAA ATA GCA ATA TTTACC TTT GGA G-3' |
| Oligo 3193 | 5'-CTA ATT AAG GGC GGC CGC KNN KNN KNN KNN KNN KNN KNN KNN KNN KNN ATA CCT TAC GAG TAC TCC AAA ACT AAT CAA TAT A- 3' |
| Oligo 3194 | 5'-TTA CTC GCG GCC CAG CCG GCC ATG GCC NNK NNK NNK NNK NNK NNK NNK NNK NNK NNK GCT CTC TAA ATA GCA ATA TTT ACC TTT GGA G-3' |
| Oligo 3198 | 5'-CAG CGT CAC GGA ATT CAT ACT TAC GAG TAC TCC AAA CTA ATC AAT ATA-3' |

OLIGONUCLEOTIDES USED TO CLONE LOXP LINKER

| | | |
|---|---|---|
| #3749 lox1 sense | 5'- TCG AGC ATA ACT TCG TAT AAT ATA AAC TAT ACG AAG TTA TCG AG- 3' |
| #3750 lox1 anti | 5'- TGC ACT CGA TAA CTT CGT ATA GTT TAT ATT ATA CGA AGT TAT GC- 3' |
| #4120 lox4 sense | 5'- TCG AGC ATA ACT TCG TAT AAC ATA GCC TAT ACG AAG TTA TCG AG- 3' |
| #4121 lox4 anti | 5'- TGC ACT CGA TAA CTT CGT ATA GGC TAT GTT ATA CGA AGT TAT GC-3' |

OLIGONUCLEOTIDES USED TO AMPLIFY THE INTRON

| | |
|---|---|
| # 3312 intron-lox back: | 5'- GAC ATG GCC ATG CCA TGG CAT GCC GCT CGA GCT CTC TAA ATA GCA ATA TTT ACC TTT GGA G-3' |
| #3463 intron-for-2 | 5'-GAG GTC GAA TTC ATA AGA ATG CGG CCG CTA AAC TAT GTG CAC TTA CCT ACG AGT ACT CCA AAA CTA ATC AAT ATA-3' |
| #3877 intron-back-3N | 5'-CAT GCC GCT CGA GCT CTC TAA ATA GCA ATA TTT ACG TTT GGA G-3' |
| #2878 intron-for-3N | 5'-CGA AGG ACA AGT GCA CTT ACG TTA CGA GTA CTC CAA AAC TAA TCA ATA TA-3' |
| INSC-BACK#4243 | 5'-CAT GCC GCT CGA GCG GCG GAG GTG GCT CTC TAA ATA GCA ATA TTT ACG TTT GGA G-3' |
| INSC-FOR#4244 | 5'-CGA AGG ACA AGT GCA CTA CCG CCT CCA CCT ACG TTA CGA GTA CTC CAA AAC TAA TCA ATA TA-3' |

Other oligonucleotides used:

| | |
|---|---|
| fd-pcr-back | 5'- GCG ATG GTT GTT GTC ATT GTC GGC- 3' |
| BamHI-for | 5' - TTC ACAAAC GAA TGG ATC CTC ATT AAA GCC AGA ATG GAA AGC GCA- 3' |

Oligonucleotides used for the construction of the vectors fdDOG-PEP, pUC19-PEP and the screening of the peptide library.

OLIGO-3249 (89 mer):
5'-CAT GAC CAC AGT GCA CAG TAA TAA TAT AAC TTC GTA TAA TGT ATA CTA TAC GAA GTT ATG CAT GCA AAT TCT ATT TCA AGG AGA CAG TC-3'

LMB2 (17 mer):
5'-GTA AAA CGA CGG CCA GT-3'

TABLE 1-continued

Oligonucleotides

OLIGO-3189 (58 mer):
5'-TTA CTC GCG GCC CAG CCG GCC ATG GCC GCT CTC TAA ATA GCA ATA TTT ACC TTT GGA G-3'

OLIGO-3193 (85 mer):
5'-CTAATTAAGGGCGGCCGCKNNKNNKNNKNNKNNKNNKNNKNNKNNATACCTTACGAGTACTCCAAAACTAATCAATATA_3'

OLIGO-3194 (88 mer):
5'_TTACTCGCGGCCCAGCCGGCCATGGCCNNKNNKNNKNNKNNKNNKNNKNNKNNKNNKGCTCTCTAAATAGCAATATTTACCTTTGGAG_3'

OLIGO-3198 (51 mer):
5'_CAGCGTCACCGGAATTCATACCTTACGAGTACTCCAAAACTAATCAATATA_3'

OLIGO-3198 (26 mer):
5'_TTAAGGAGAGGTCCGACTATATCTTA_3' pelBBACK (20 mer):
5'_GAAATACCTATTGCCTACGG_3'

OLIGO-4226 (26 mer):
5'_GCGTGGTTAGGTCCATGTCCGTCAGC_3' fdSEQ1 (17 mer):
5'_GAATTTTCTGTATGAGG_3'

OLIGO-3870 (17 mer):
5'_TCCTTTAGTTGTTCCTT_3'

OLIGO-4445 (17 mer):
5'_ACTTCGTACTGAACGGC_3'

OLIGO-3358 (21 mer):
5'_GAAGTGATGCAACACTGGAGC_3'

N means an equimolar mixture of all 4 bases and K an equimolar mixture of G and T.

---

We claim:

1. A DNA construct comprising a first exon sequence of nucleotides encoding a first peptide or polypeptide, a second exon sequence of nucleotides encoding a second peptide or polypeptide and a third sequence of nucleotides between the first and second sequences encoding a heterologous intron between RNA splice sites and a site-specific recombinase recognition sequence within the intron, the exons together encoding a product peptide or polypeptide.

2. A DNA construct according to claim 1 wherein the product peptide or polypeptide comprises a member of a specific binding pair (sbp).

3. A DNA construct according to claim 2 wherein the sbp member comprises a binding domain able to bind complementary sbp member.

4. A DNA construct according to claim 3 wherein the binding domain is an immunoglobulin antigen-binding site.

5. A DNA construct according to claim 4 wherein the product peptide or polypeptide is a scFv antibody fragment which comprises a VH domain linked to a VL domain via a peptide linker which allows the VH and VL domains to associate to form the antigen-binding site.

6. A DNA construct according to claim 5 wherein the intron is selected from a group consisting of a self-splicing group I intron and a self-splicing group II intron.

7. A DNA construct according to claim 5 wherein the product peptide or polypeptide comprises a surface component of an organism.

8. A DNA construct according to claim 5 which is a vector further comprising nucleic acid for expression of the product peptide or polypeptide.

9. A method of producing a product peptide or polypeptide which comprises a combination of a first peptide or polypeptide component and a second peptide or polypeptide component, the method comprising:
   providing a DNA construct according to claim 8;
   transcribing DNA of the construct into RNA;
   causing or allowing splicing of nucleotides of the third sequence to produce an RNA molecule encoding the product peptide or polypeptide;
   translating the RNA molecule into the product peptide or polypeptide.

10. A method according to claim 9 wherein a plurality of DNA constructs is provided for transcription, splicing and translation.

11. A method according to claim 10 wherein, following said translation, product peptide or polypeptide of interest is selected or isolated from other peptides or polypeptides present.

12. A plurality of DNA constructs according to claim 5 collectively encoding a repertoire of product peptide or polypeptides wherein each product peptide or polypeptide in the repertoire has a different amino acid sequence.

13. A plurality of host cells comprising a plurality of DNA constructs according to claim 12.

14. A DNA construct according to claim 5 wherein transcription of said construct leads to mRNA having nucleotides corresponding to nucleotides of said RNA splice sites which encode and are translatable into amino acids of the peptide linker of said scFv antibody fragment.

15. A DNA construct according to claim 1 wherein the product peptide or polypeptide is selected from the group consisting of a T cell receptor $V_\alpha$ and a T cell receptor $V_\beta$ domain, a T cell receptor/antibody fusion, a T cell receptor/antibody fragment fusion, a receptor binding peptide, an enzyme, a multiple domain protein, an amino acid sequence variant of said peptide or polypeptide and a derivative of said peptide or polypeptide.

16. A DNA construct according to claim 1 wherein the product peptide comprises a binding domain able to bind a complementary sbp member.

17. A DNA construct according to claim 16 wherein one of said first and second peptides or polypeptides comprises an antibody fragment.

18. A DNA construct according to claim 17 wherein the antibody fragment is selected from the group consisting of VH, VL, CH, CL, VH—CH and VL—CL.

19. DNA construct according to claim 16 wherein the first and/or second peptides or polypeptides comprise an amino acid sequence encoded by a synthetic nucleotide sequence.

20. A DNA construct according to claim 16 wherein the intron is selected from a group consisting of a self-splicing group I intron and a self-splicing group II intron.

21. A DNA construct according to claim 16 wherein the product peptide or polypeptide comprises a surface component of an organism.

22. A DNA construct according to claim 16 which is a vector further comprising nucleic acid for expression of the product peptide or polypeptide.

23. A method of producing a product peptide or polypeptide which comprises a combination of a first peptide or polypeptide component and a second peptide or polypeptide component, the method comprising:

providing a DNA construct according to claim 22;

transcribing DNA of the construct into RNA;

causing or allowing splicing of nucleotides of the third sequence to produce an RNA molecule encoding the product peptide or polypeptide;

translating the RNA molecule into the product peptide or polypeptide.

24. A method according to claim 23 wherein a plurality of DNA constructs is provided for transcription, splicing and translation.

25. A method according to claim 24 wherein, following said translation, product peptide or polypeptide of interest is selected or isolated from other peptides or polypeptides present.

26. A plurality of DNA constructs according to claim 16 collectively encoding a repertoire of product peptide or polypeptides wherein each product peptide or polypeptide in the repertoire has a different amino acid sequence.

27. A plurality of host cells comprising a plurality of DNA constructs according to claim 26.

28. A DNA construct according to claim 1 wherein the intron is selected from a group consisting of a self-splicing group I intron and a self-splicing group II intron.

29. A DNA construct according to claim 28 wherein the self-splicing intron is obtainable from *Tetrahymena thermophila* nuclear pre-rRNA.

30. A DNA construct according to claim 1 wherein the site-specific recombinase recognition sequence is the loxP sequence obtainable from coliphage P1, or a mutant or derivative of said loxP sequence.

31. A DNA construct according to claim 1 wherein the product peptide or polypeptide comprises a surface component of an organism.

32. A DNA construct according to claim 31 wherein the organism is a bacteriophage.

33. A DNA construct according to claim 32 wherein the bacteriophage is selected from a group consisting of fd and M13.

34. A DNA construct according to claim 33 wherein the surface component is the gene III product.

35. A DNA construct according to claim 1 which is a vector further comprising nucleic acid for expression of the product peptide or polypeptide.

36. A DNA construct according to claim 35 further comprising nucleic acid for secretion of the product peptide or polypeptide.

37. A DNA construct according to claim 36 wherein said vector is selected from a group consisting of a plasmid, a phage, and a phagemid vector.

38. A method of producing a product peptide or polypeptide which comprises a combination of a first peptide or polypeptide component and a second peptide or polypeptide component, the method comprising:

providing a DNA construct according to claim 35;

transcribing DNA of the construct into RNA;

causing or allowing splicing of nucleotides of the third sequence to produce an RNA molecule encoding the product peptide or polypeptide;

translating the RNA molecule into the product peptide or polypeptide.

39. A method according to claim 38 wherein transcription, splicing and translation take place in vitro.

40. A method according to claim 39 wherein transcription, splicing and translation take place in vivo.

41. A method according to claim 40 wherein transcription, splicing and translation take place in *E. coli* cells.

42. A method according to claim 38 wherein a plurality of DNA constructs is provided for transcription, splicing and translation.

43. A method according to claim 42 wherein, following said translation, product peptide or polypeptide of interest is selected or isolated from other peptides or polypeptides present.

44. A method according to claim 38 wherein, following said translation, product peptide or polypeptide of interest is selected or isolated from other peptides or polypeptides present.

45. A host cell comprising a DNA construct according to claim 1.

46. A plurality of DNA constructs according to claim 1 collectively encoding a repertoire of product peptide or polypeptides wherein each product peptide or polypeptide in the repertoire has a different amino acid sequence.

47. A population of host cells comprising a plurality of DNA constructs according to claim 46.

48. An isolated nucleic acid construct consisting essentially of a self-splicing intron with a site-specific recombinase recognition sequence within the intron.

49. A nucleic acid construct according to claim 48 wherein the self-splicing intron is obtainable from *Tetrahymena thermophila* nuclear pre-rRNA.

50. A nucleic acid construct according to claim 48 wherein the site-specific recombinase recognition sequence is the loxP sequence obtainable from coliphage P1 or a mutant or derivative of said loxP sequence.

* * * * *